United States Patent
Deutsch et al.

(10) Patent No.: US 9,957,314 B2
(45) Date of Patent: May 1, 2018

(54) REGENERATION AND REPAIR OF MESENCHYMAL TISSUE USING AMELOGENIN

(71) Applicants: Yissum Research Development Company of the Hebrew University of Jerusalem Ltd., Jerusalem (IL); Hadasit Medical Research Services and Development Ltd., Jerusalem (IL)

(72) Inventors: Dan Deutsch, Motza Elite (IL); Amir Haze, Modiln (IL); Anat Blumenfeld, Mevaseret Zion (IL)

(73) Assignees: HADASIT MEDICAL RESEARCH SERVICES AND DEVELOPMENT LTD., Jerusalem (IL); YISSUM RESEARCH DEVELOPMENT COMPANY OF THE HEBREW UNIVERSITY OF JERUSALEM LTD., Jerusalem (IL)

( * ) Notice: Subject to any disclaimer, the term of this patent is extended or adjusted under 35 U.S.C. 154(b) by 683 days.

(21) Appl. No.: 14/471,262

(22) Filed: Aug. 28, 2014

(65) Prior Publication Data

US 2014/0364372 A1 Dec. 11, 2014

Related U.S. Application Data

(63) Continuation-in-part of application No. 14/116,796, filed as application No. PCT/IL2012/050163 on May 9, 2012, now abandoned.

(60) Provisional application No. 61/483,909, filed on May 9, 2011, provisional application No. 61/871,619, filed on Aug. 29, 2013.

(51) Int. Cl.
*A61K 39/00* (2006.01)
*C07K 14/00* (2006.01)
*C07K 14/78* (2006.01)
*A61K 38/39* (2006.01)

(52) U.S. Cl.
CPC .............. *C07K 14/78* (2013.01); *A61K 38/39* (2013.01)

(58) Field of Classification Search
None
See application file for complete search history.

(56) References Cited

U.S. PATENT DOCUMENTS

| | | | |
|---|---|---|---|
| 6,677,306 B1 * | 1/2004 | Veis .................. | C07K 14/78 424/422 |
| 2003/0003128 A1 * | 1/2003 | Chiarelli ............. | A61C 8/0012 424/423 |
| 2011/0003745 A1 | 1/2011 | Fehr et al. | |
| 2014/0073765 A1 | 3/2014 | Deutsch et al. | |

FOREIGN PATENT DOCUMENTS

| | | |
|---|---|---|
| EP | 0337967 | 5/1993 |
| EP | 1862143 | 12/2007 |
| WO | WO 00/06734 | 2/2000 |
| WO | WO 00/53197 | 9/2000 |
| WO | WO 2011/030185 | 3/2011 |
| WO | WO 2012/153333 | 11/2012 |

OTHER PUBLICATIONS

Messenger et al Z( J of Tissue Enginer, 2010, v.4 pp. 96-104.*
International Preliminary Report on Patentability dated Jul. 15, 2013 From the International Preliminary Examining Authority Re. Application No. PCT/IL2012/050163.
International Search Report and the Written Opinion dated Oct. 5, 2012 From the International Searching Authority Re.: Application No. PCT/IL2012/050163.
Written Opinion dated Apr. 25, 2013 From the International Preliminary Examining Authority Re. Application No. PCT/IL2012/050163.
Deutsch et al. "Amelogenin, A Major Structural Protein in Mineralizing Enamel, Is Also Expressed in Soft Tissues: Brain and Cells of the Hematopoietic System", European Journal of Oral Sciences, 114(Suppl.1): 183-189, 2006.
Gruenbaum-Cohen et al. "Amelogenin in Cranio-Facial Development: The Tooth as a Model to Study the Role of Amelogenin During Embryogenesis", Journal of Experimental Zoology, Part B: Molecular and Developmental Evolution, 312B(5): 445-457, Jul. 15, 2009.
Haze et al. "Amelogenin Expression in Long Bone and Cartilage Cells and in Bone Marrow Progenitor Cells", The Anatomical Record, 290: 455-460, 2007.
Haze et al. "Regeneration of Bone and Periodontal Ligament Induced by Recombinant Amelogenin After Periodontitis", Journal of Cellular and Moleculer Medicine, XP002683976, 13(6): 1110-1124, Jun. 2009. Abstract.
Huang et al. "Effects of Human Full-Length Amelogenin on the Proliferation of Human Mesenchymal Stem Cells Derived from Bone Marrow", Cell and Tissue Research, XP019860977, 342(2): 205-212, Oct. 22, 2010. Abstract.
Messenger "The Use of Emdogain for Cruciate Ligament Tissue Engineering", IADR Pan European Federation 2006, Dublin, Ireland, Sep. 13-16, 2006, Seq #62—Mineralised Tissue: Enamel and Hydroxyyapatite, Dentine and Bone: Chemistry, Structure and New Technologies, # 0533, Sep. 15, 2006.
Taylor et al. "High Yield of Biologically Active Recombinant Human Amelogenin Using the Baculovirus Expression System", Protein Exporession and Purification, 45: 43-53, 2006.
Restriction Official Action dated Jun. 26, 2015 From the U.S. Appl. No. 14/116,796.
https://www.ncbi.nlm.nih.gov/protein/NP_001133.1, "amelogenin, X isoform isoform 1 precursor [*Homo sapiens*]", NCBI Reference Sequence:NP_001133.1, Aug. 14, 2017.

(Continued)

*Primary Examiner* — Michail A Belyavskyi
(74) *Attorney, Agent, or Firm* — Browdy and Neimark, PLLC

(57) ABSTRACT

A method of treating an injury to hyaline cartilage in a subject in need thereof. The method comprises administering to the subject a therapeutically effective amount of amelogenin.

11 Claims, 11 Drawing Sheets
(11 of 11 Drawing Sheet(s) Filed in Color)

(56) References Cited

OTHER PUBLICATIONS https://www.ncbi.nlm.nih.gov/protein/NP_872621.1, "amelogenin, X isoform isoform 3 [*Homo sapiens*]", NCBI Reference Sequence:NP_872621.1, Oct. 1, 2017.

* cited by examiner

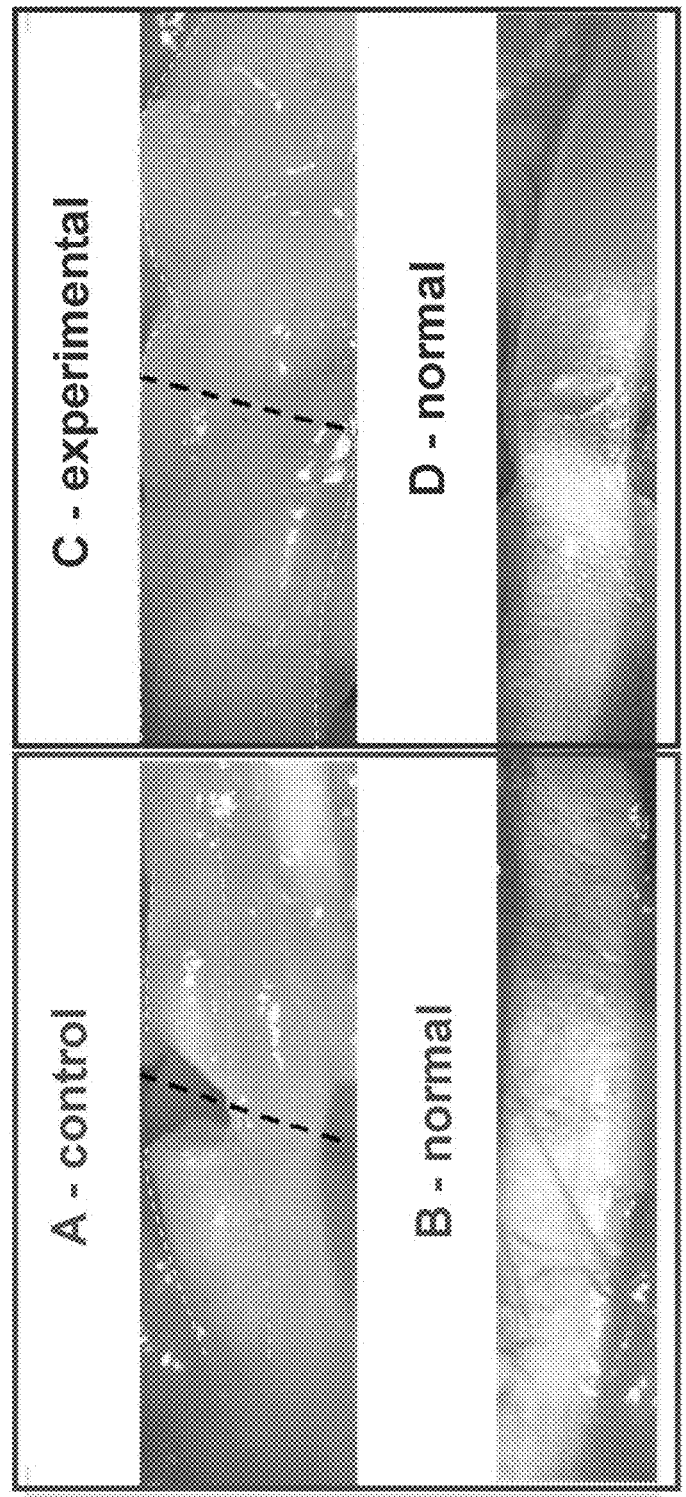

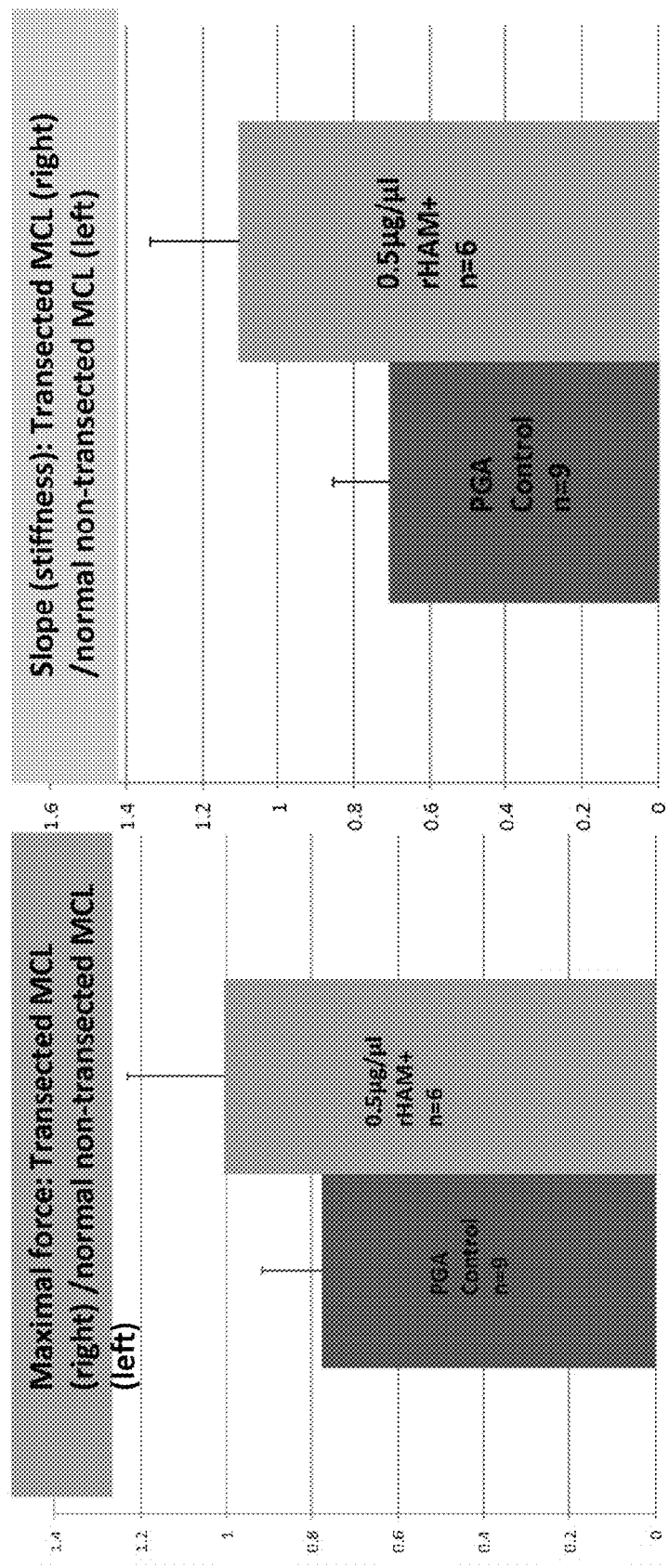

L- Ligament, FG- Filled Gap

FIG. 6A
Initial Defect | 12 weeks after defect creation
Control- PGA carrier only | Experimental- 0.5mg/ml rHAM+
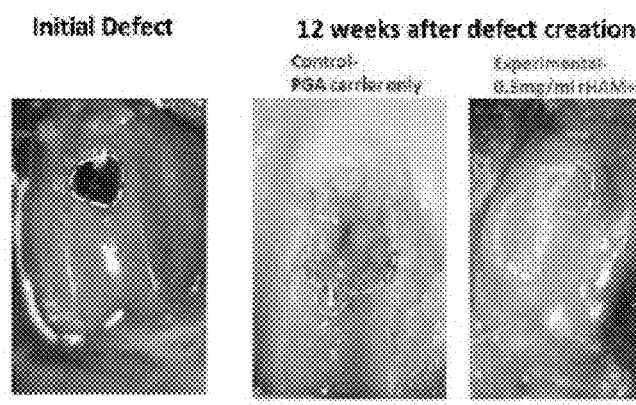
FIG. 6B
Defect area / Articular surface area
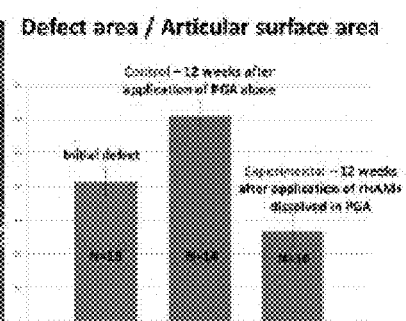
FIG. 6C
Control- PGA only | Experimental- 0.5mg/ml rHAM+
*H&E Stain:*
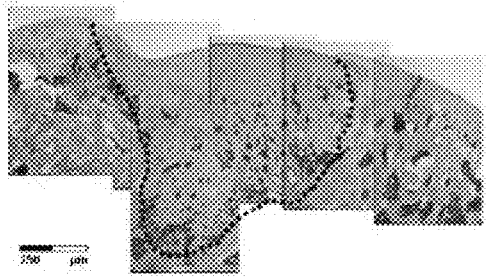 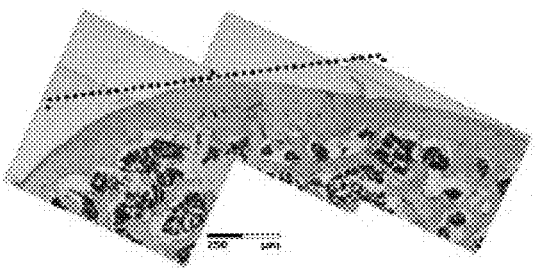
*Toluidin Blue Stain:*
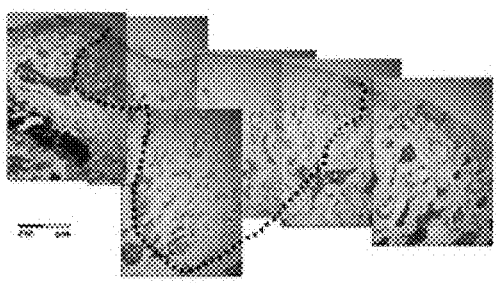 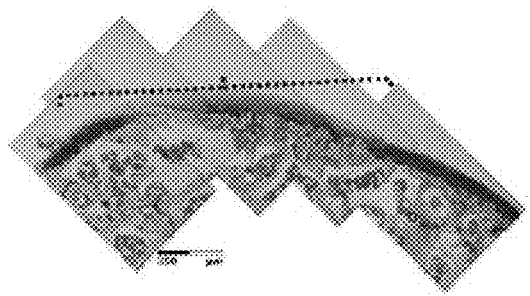
*Immunohistochemistry for Collagen II:*
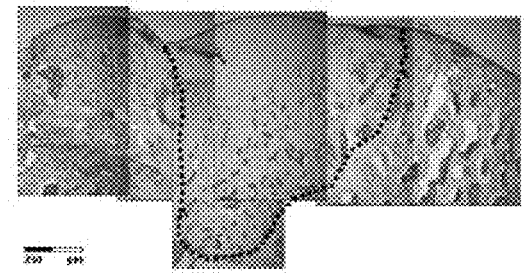 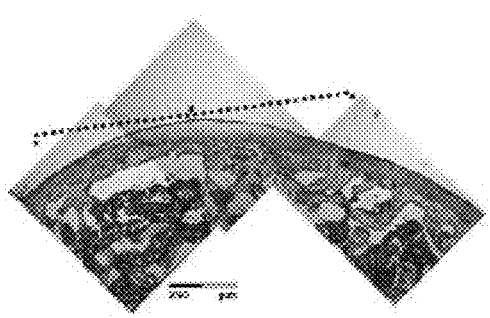

CD105 (MSC marker) expression - 4 days after the osteochondral fracture creation

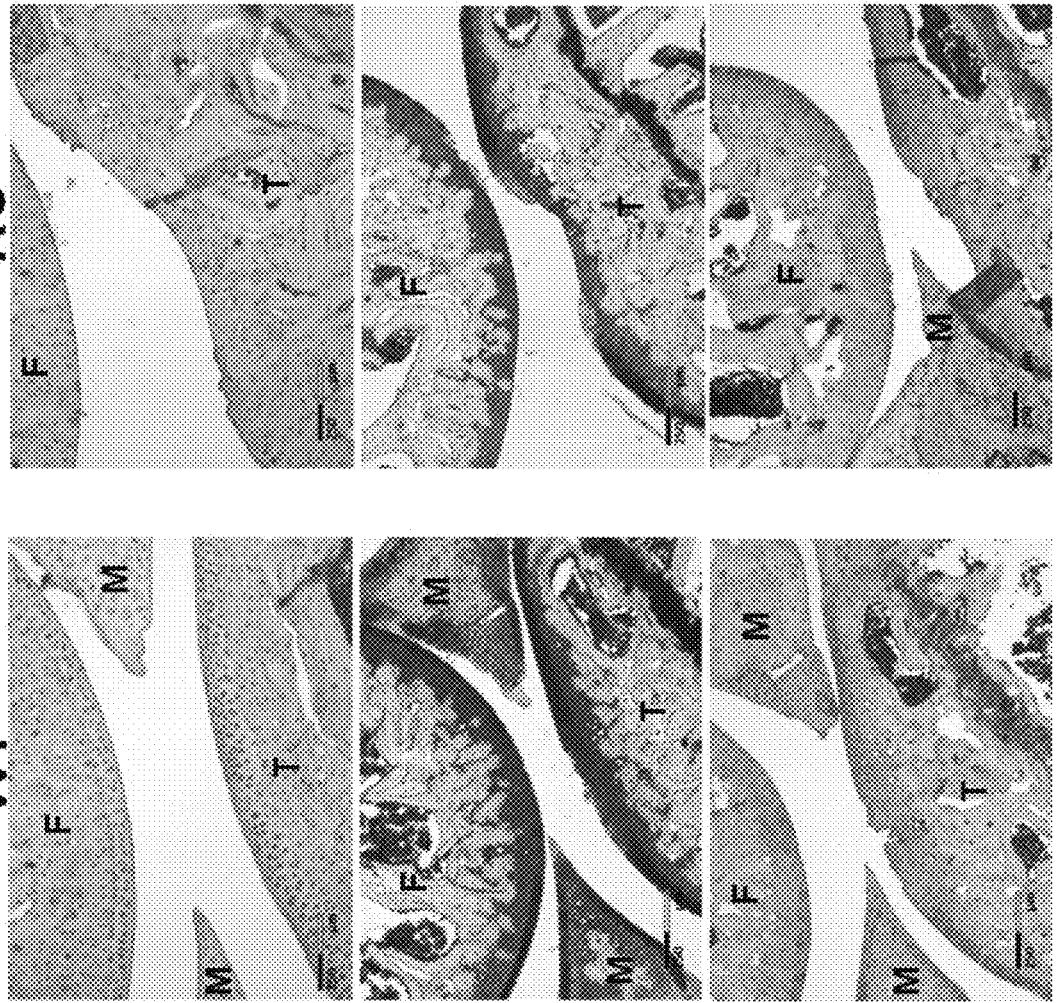

REGENERATION AND REPAIR OF MESENCHYMAL TISSUE USING AMELOGENIN

RELATED APPLICATIONS

This application is a Continuation-in-Part (CIP) of U.S. patent application Ser. No. 14/116,796 filed on Nov. 11, 2013, which is a National Phase of PCT Patent Application No. PCT/IL2012/050163 having International filing date of May 9, 2012, which claims the benefit of priority under 35 USC § 119(e) of U.S. Provisional Patent Application No. 61/483,909 filed on May 9, 2011.

This application also claims the benefit of priority under 35 USC § 119(e) of U.S. Provisional Patent Application No. 61/871,619 filed on Aug. 29, 2013.

The contents of the above applications are all incorporated by reference as if fully set forth herein in their entirety.

SEQUENCE LISTING STATEMENT

The ASCII file, entitled 60207SequenceListing.txt, created on Aug. 28, 2014, comprising 2,009 bytes, submitted concurrently with the filing of this application is incorporated herein by reference.

FIELD AND BACKGROUND OF THE INVENTION

The present invention, in some embodiments thereof, relates to the use of amelogenin for enhancing the regeneration of hyaline cartilage, and more specifically articular cartilage.

Cartilage is a mesenchymal tissue; mesenchymal stem cells (MSCs) differentiate to form matrix secreting chondroblasts. Chondroblasts become mature chondrocytes when the matrix encircles them. Depending on the composition of the matrix, cartilage in human body is classified into elastic, fibro-cartilage, fibro-elastic and hyaline cartilage. The gliding surfaces of the synovial joint are covered with a specialized type of hyaline cartilage, termed articular cartilage, which by itself is composed of four zones; superficial, transitional, middle and calcified cartilage zone. Each zone has its unique and characteristic structure of chondrocytes and matrix arrangement, which is crucial for the function of the whole tissue. The superficial zone, the thinnest of all layers, is composed of flattened ellipsoid cells. They lie parallel to the joint surface, and are covered by a thin film of synovial fluid, called 'lubricin'. This protein is responsible for providing an ultimate gliding surface to the articular cartilage. Chondrocytes in this zone synthesize high concentrations of collagen and low concentrations of proteoglycans, hence, it is the highest water content zone within the articular cartilage. Parallel arrangement of the fibrils are responsible for providing the greatest tensile and shear strength. Disruption of this zone alters the mechanical properties of the articular cartilage and thus contributes to the development of osteoarthritis. This layer also acts as a filter for large macro-molecules, thereby protecting the cartilage from synovial tissue immune system. In the transitional zone the cell density is lower, with predominantly spheroid shaped cells, embedded in abundant extracellular matrix. The large diameter collagen fibers are randomly arranged in this zone. In the middle zone cells are arranged perpendicular to the surface and are spherical in shape. This zone contains the largest diameter of collagen fibrils and the highest concentration of proteoglycans. However, the cell density is lowest in this zone. The calcified cartilage zone is mineralized, contains small volume of cells embedded in a calcified matrix and thus showing a very low metabolic activity. The chondrocytes in this zone express hypertrophic phenotype. These cells are unique since they synthesize type X collagen, responsible for providing important structural integrity and a shock absorber along with the subchondral bone.

Hyaline cartilage provides a low-friction gliding surface, with increased compressive strength and is known to be wear-resistant under normal conditions. Hyaline articular cartilage is aneural, avascular and alymphatic structure. Chondrocytes, the mature cartilage cell (1-5% of its volume), receive their nutrition by diffusion through the matrix. Regeneration of hyaline cartilage is a major scientific challenge; a typical response of tissue to injury follows a cascade of necrosis, inflammation, repair and scar remodeling. The most important determinant of the healing process is the vascular phase of this cascade. Hyaline cartilage, being an avascular structure, lacks the ability to generate this vital response, leading to very low intrinsic reparative capability. When cartilage do heal, fibrocartilage is formed, which lacks the unique structural arrangement and biochemical composition of the hyaline cartilage, hence is inferior clinically and eventually leads to joint degeneration.

Physicians and scientists have sought different ways to repair or regenerate articular surface of synovial joint following traumatic damage or degeneration of the cartilage. The variety of surgical treatments based on different methods aim to increase the quantity of cells capable to differentiate into chondrocytes at the injured site. Penetration of subchondral bone is among the oldest and still the most commonly used method to stimulate regeneration of neo-cartilage. Penetration of subchondral bone plate disrupts the subchondral blood vessels. This leads to the formation of a 'super clot' or fibrin clot on the surface of a chondral defect. If the defect is protected from loading at this stage, then primitive bone marrow mesenchymal stem cells migrate into the super clot, to proliferate and differentiate into cells resembling chondrocytes morphologically. A newer modality for repair of osteochondral defects is the use of autologus culture expanded chondrocytes or bone marrow mesenchymal stem cells, implanted into the defect in order to regenerate the tissue. In spite of efforts to produce different treatment methods, none of the above has been able to regenerate a neo-cartilage which is similar in structure and functions to that of a native articular cartilage.

Osteoarthritis (OA) is a chronic degenerative joint disease that progressively causes loss of joint function. The morphologic and biochemical manifestations of OA are; articular cartilage breakdown, subchondral sclerosis, osteophyte formation, bone marrow lesions and alterations of the synovium. The altered biomechanics seen in OA induce and potentiate biochemical changes. Key events occurring in cartilage during the pathogenesis of OA include an imbalance of metabolic and degradative signals. Chondrocytes, as well as synovial cells, of OA patients produce increased levels of inflammatory cytokines, such as interleukin-1$\beta$ (IL-1b) and tumor necrosis factor-$\alpha$ (TNF-$\alpha$), which in turn decrease anabolic collagen synthesis and increase catabolic (including matrix metalloproteinases—MMPs) and other inflammatory mediators such as IL-8, IL-6, and prostaglandin E2. In addition, mechanical stress increases nitric oxide production by chondrocytes as well as nitric oxide synthetase expression. These reactive oxygen species have been implicated indirectly in promoting chondrocyte apoptosis, catabolic processes and matrix degradation.

The amelogenins are a major component of the developing extracellular enamel matrix proteins, produced by the ameloblast cells and play a major role in the biomineralization and structural organization of enamel (Robinson et al. 1998). The human amelogenin gene contains 7 exons, which undergo alternative mRNA splicing. The most abundant amelogenin lacks the internal region encoded by exon 4, is termed HX175 in human, which corresponds to isoform M180 in mice. The relatively large number of amelogenin alternatively spliced mRNA translated polypeptides and the fact that amelogenin is expressed in different tissues (calcifying and soft tissues) and of different embryonic origin, possibly reflect different functions of amelogenin.

Amelogenin was shown to be expressed in periodontal ligament (PDL) cells, in long bone cells; osteocytes, osteoblasts and osteoclasts, in cartilage chondrocytes and differentially in growth plate cells. In addition, amelogenin was identified in long bone marrow stromal cells, some of which are multi-potent stem cells (Haze et al. 2007). Furthermore, in the normal uninjured animal, amelogenin expression is increased at sites of high activity and remodeling of ligaments and bones (Haze et al. 2009). Amelogenin expression was also identified in cells of non-mineralizing tissues such as brain and eye in embryonic and postnatal tissues (Deutsch et al. 2006, Gruenbaum-Cohen et al. 2008).

Recombinant human amelogenin has been shown to be beneficial for the treatment of periodontitis (Haze et al. 2009).

International Patent Application WO2011/030185 teaches a cell guiding scaffold which according to one embodiment may comprise amelogenin as one of its active agents for inducing periodontal tissue regeneration. The scaffold may be used for joint ligament regeneration as well.

International Patent Application WO 00/06734 teaches that amelogenin is useful for generation of bone and cartilage. More specifically, this application teaches that it causes an up-regulation in type II collagen and has no effect or negative effect on type I collagen.

U.S. Patent Application Publication Nos. 20100093632 and 20030077291 teach the use of amelogenin for the treatment of inflammatory disorders.

U.S. Patent Application Publication No. 20140073765 teaches the use of amelogenin for the treatment of cartilage injuries.

Additional background material includes European Patent Publication Nos. 0337967, 1862143 and 0053197 and US Patent Application No. 20110003745.

SUMMARY OF THE INVENTION

According to an aspect of some embodiments of the present invention there is provided a method of treating an injury to or a disease of a skeletal joint ligament or tendon in a subject in need thereof, the method comprising contacting the skeletal joint ligament or tendon of the subject with a therapeutically effective amount of amelogenin, wherein the amelogenin is not comprised in a scaffold, thereby treating the injury to or disease of the skeletal joint ligament or tendon.

According to an aspect of some embodiments of the present invention there is provided a method of treating an injury to or a disease of a skeletal muscle ligament or tendon in a subject in need thereof, the method comprising contacting the skeletal muscle ligament or tendon of the subject with a therapeutically effective amount of mesenchymal stem cells (MSCs) which have been genetically modified to express amelogenin, thereby treating the injury to or disease of the skeletal joint ligament or tendon.

According to an aspect of some embodiments of the present invention there is provided a method of treating osteoarthritis, in a subject in need thereof, the method comprising administering to the subject a therapeutically effective amount of amelogenin, thereby treating the osteoarthritis.

According to an aspect of some embodiments of the present invention there is provided a method of enhancing regeneration of cardiac tissue, the method comprising contacting the cardiac tissue with amelogenin, thereby enhancing regeneration of the cardiac tissue.

According to an aspect of some embodiments of the present invention there is provided a method of treating a disease associated with cardiac tissue degeneration in a subject in need thereof, the method comprising administering to the subject a therapeutically effective amount of amelogenin, thereby treating the disease associated with cardiac tissue degeneration.

According to an aspect of some embodiments of the present invention there is provided a method of treating an injury to, or a disease of, mesenchymal tissue in a subject in need thereof, the method comprising administering to the subject a therapeutically effective amount of mesenchymal stem cells (MSCs) which have been genetically modified to express amelogenin, with the proviso that the mesenchymal tissue does not comprise periodontal tissue, thereby treating the injury to or disease of the mesenchymal tissue.

According to an aspect of some embodiments of the present invention there is provided a method of treating an injury associated with a meniscus, labrum and spinal intervertebral disc in a subject in need thereof, the method comprising contacting the meniscus, labrum or disc of the subject with a therapeutically effective amount of amelogenin, thereby treating the injury to or disease of the meniscus, labrum and spinal disc.

According to some embodiments of the invention, the amelogenin is expressed in a population of MSCs.

According to some embodiments of the invention, the amelogenin is human amelogenin.

According to some embodiments of the invention, the amelogenin comprises an amino acid sequence as set forth in SEQ ID NO: 1.

According to some embodiments of the invention, the mesenchymal tissue is selected from the group consisting of ligament, tendon, cartilage, bone, muscle and fat.

According to some embodiments of the invention, the MSCs are isolated from bone marrow tissue.

According to some embodiments of the invention, the amelogenin is expressed from an adenoviral vector.

According to another aspect of the present invention there is provided a method of treating an injury to hyaline cartilage in a subject in need thereof, comprising administering to the subject a therapeutically effective amount of amelogenin, thereby treating the injury to the hyaline cartilage.

According to some embodiments of the invention, the injury is to the meniscus, labrum or spinal intervertebral disc.

According to some embodiments of the invention, the injury is a tear.

According to some embodiments of the invention, the hyaline cartilage comprises articular cartilage.

According to some embodiments of the invention, the amelogenin is expressed in a population of mesenchymal stem cells (MSCs).

According to some embodiments of the invention, the amelogenin is human amelogenin.

According to some embodiments of the invention, the amelogenin comprises an amino acid sequence as set forth in SEQ ID NO: 1.

According to some embodiments of the invention, the MSCs are isolated from bone marrow tissue. According to some embodiments of the invention, the amelogenin is expressed from an adenoviral vector.

According to some embodiments of the invention, the amelogenin is a recombinant amelogenin.

According to some embodiments of the invention, the amelogenin is administered arthroscopically.

According to another aspect of the present invention there is provided a method of treating arthritis in a subject in need thereof, the method comprising administering to the subject a therapeutically effective amount of amelogenin, thereby treating arthritis in the subject.

According to some embodiments of the invention, the arthritis comprises an arthritic joint.

According to some embodiments of the invention, the amelogenin is expressed in a population of mesenchymal stem cells (MSCs).

According to some embodiments of the invention, the amelogenin is human amelogenin.

According to some embodiments of the invention, the amelogenin comprises an amino acid sequence as set forth in SEQ ID NO: 1.

According to some embodiments of the invention, the MSCs are isolated from bone marrow tissue.

According to some embodiments of the invention, the amelogenin is expressed from an adenoviral vector.

According to some embodiments of the invention, the amelogenin is a recombinant amelogenin.

According to some embodiments of the invention, the amelogenin is administered endoscopically.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawings will be provided by the Office upon request and payment of the necessary fee.

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-D are photographs illustrating transected medial collateral ligament (MCL) two weeks after operation, the dotted yellow lines mark the borders of the ligament. (A) Transected MCL, treated with PGA carrier only (control) as compared with (B) non-transected MCL, from the contralateral leg. (C) Transected MCL, treated with rHAM$^+$ dissolved in PGA (experimental) as compared with (D) non-transected MCL, from the contralateral leg. The dotted line marks the transection zone. The results indicate closure of the gap between the stumps, already two weeks following treatment with rHAM$^+$ dissolved in PGA (experimental), while no such recovery was demonstrated after treatment with PGA carrier only (control).

FIGS. 2A-B are graphs illustrating maximal force comparison (A) and stiffness (slope) comparison (B) between the transected MCL to the non-transected normal MCL from the contra-lateral leg of each rat. 15 rats were operated; in 6 rats 0.5 µg/µl rHAM$^+$ dissolved in PGA carrier was applied to the transected MCL-experimental (n=6) while in 9 rats PGA carrier only was applied to the transected MCL-control (n=9). 12 weeks after the transection the rat was killed and the mechanical properties of the two legs (non-transected and transected) were compared. The difference between the experimental and control groups was significant (A. $p<0.03$, B. $p<0.01$).

Figure 3A:
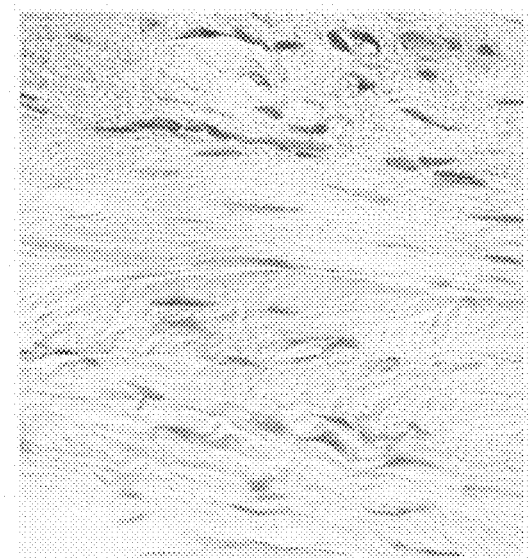
Figure 3B:
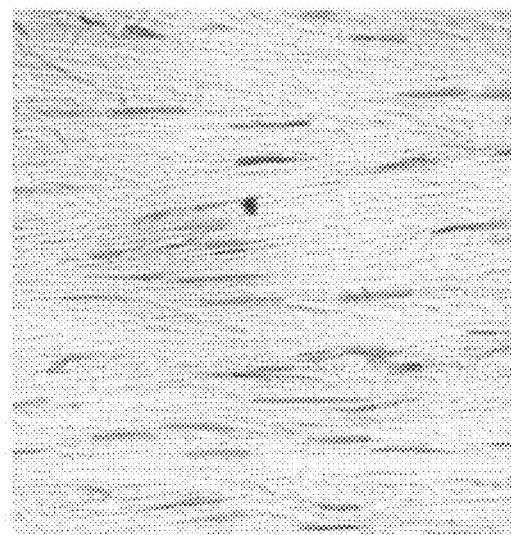
Figure 3C:

FIGS. 3A-C are photographs illustrating H&E staining of the ligaments 12 weeks after the operation: (A)=normal non-transected ligament, (B)=0.5 µg/µl rHAM$^+$ dissolved in PGA (experimental), (C)=PGA only (control), showing that the ligament fibers in experimental tissue are arranged in an elongated orientation similar to the normal non-transected ligament. In the control PGA there is no spatial arrangement of the fibers, similar to findings in a scar tissue. The experimental and control tissues seems much cellular as compared to the normal non-transected ligament.

Figure 4C:
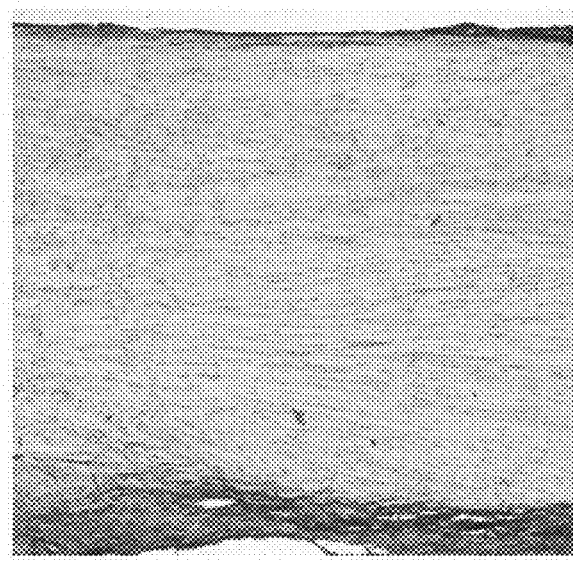
Figure 4B:
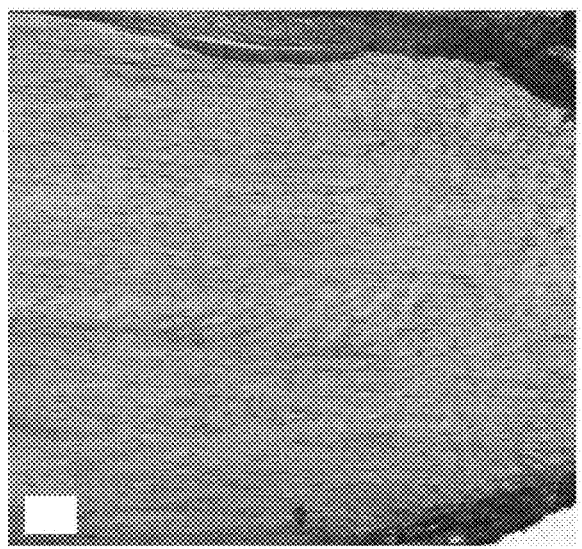
Figure 4A:
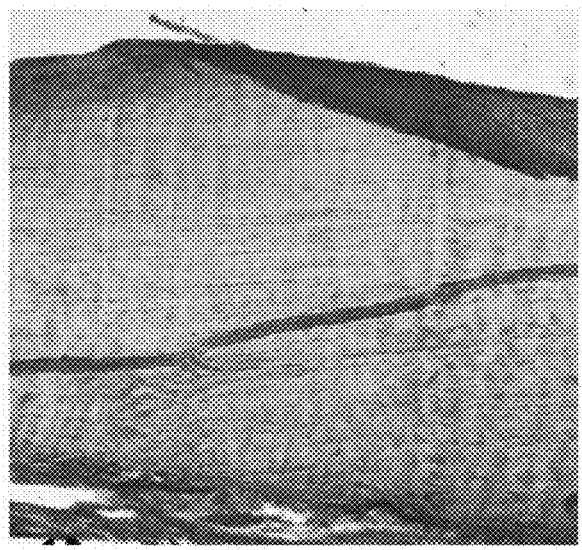

FIGS. 4A-C are photographs illustrating immunohistochemical staining of collagen 1 (brown staining) in the ligaments 12 weeks following the operation: (A)=normal non-transected ligament, (B)=0.5 µg/µl rHAM$^+$ dissolved in PGA (experimental), (C)=PGA only (control). The photographs show that there is much more collagen 1 expression in the experimental ligament as compared to the control PGA treated ligament. Collagen 1 is the major protein in ligament which provides the mechanical properties and strength of normal ligament.

Figures 5A, 5B, 5C:
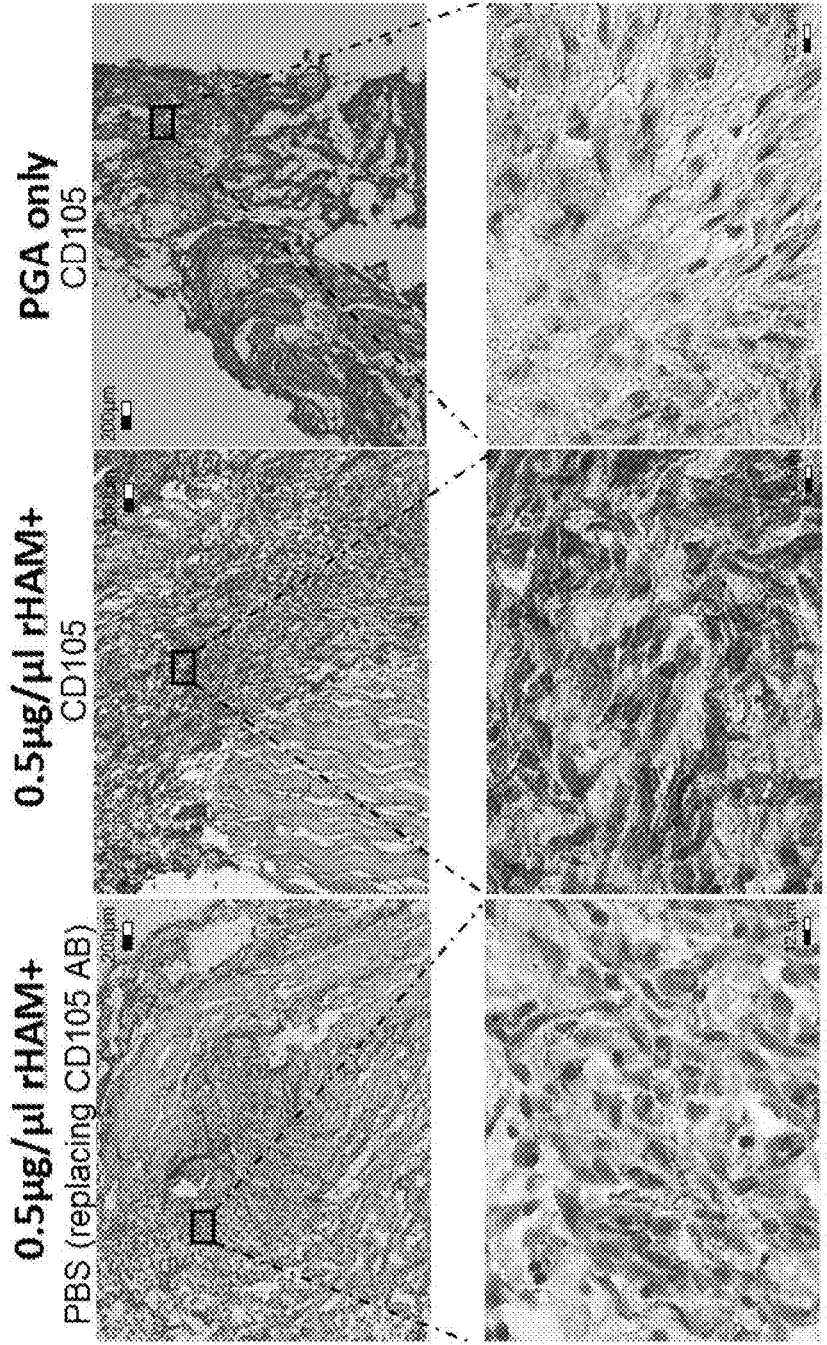

FIGS. 5A-C are photographs illustrating immunohistochemical staining of the mesenchymal stem cell marker CD105 (brown staining) in the ligaments 4 days following transection. The dotted yellow line marks the borders of the transected ligament, all the other tissue is inflammatory tissue filling the gap between the ligament stumps. (A, B)—transected ligament treated with 0.5 µg/µl rHAM$^+$ dissolved in PGA (experimental), (C)—treatment with PGA only (control). The photographs show that there are a high number of cells expressing CD105, indicating recruitment of MSCs in the filled gap of the experimental ligament, while almost no CD105 recruited MSCs are detected in the filled gap of the control ligament.

FIGS. 6A-C are photographs illustrating the regeneration of rat knee osteochondreal fracture (OCF) induced by rHAM$^+$. (A)—Photographs illustrating the size of the OCF (marked by the dotted yellow line) at the femoral trochlea at the time of the operation, and 12 weeks after operation. In the control-application of PGA carrier only, the size of the defect increased and post-traumatic osteoarthritic changes are detected through most of the trochlea area. In the experimental-application of 0.5 µg/µl rHAM$^+$ dissolved in PGA, the fracture site can hardly be detected and no arthritic changes are seen. (B)—Statistical analyses of the results 12 weeks after the operation, show significant increase in the damaged area in the control versus the initial fracture (p<0.001), representing the severe arthritic changes demonstrated in FIG. 6A. There was a significant decrease in the damaged area in the experimental group treated with 0.5 µg/µl rHAM⁺, compared to the initial defect (P<0.05) and to the PGA control (P<0.01). N=the number of rats in each group. (C)—Histological structural and compositional analyses of the fracture site 12 weeks after the operation. The size of the fracture and damaged area is marked by the dotted line. In the experimental figures the dotted line marks the area of the initial fracture. The structural analysis (Hematoxylline & Eosin staining) shows that in the control the damaged area is big and completely filled with fibrotic scar tissue. On the other hand in the experimental group treated with 0.5 µg/µl rHAM⁺, there is complete regeneration of the fractured subchondral bone and regeneration of a cartilaginous tissue, which begun to arrange in layers resembling hyaline cartilage. It seems that the regeneration process initiated at the sides of the fracture and advanced toward the center of the damaged area. Initial osteoarthritic changes are characterized by depletion in proteoglycans in the hyaline cartilage. In the PGA control the amount of proteoglycans in the tissue (stained purple or deep blue with toluidine blue) seems to be significantly lower than in the experimental group, suggesting an advanced and rapid osteoarthritic changes, while in the experimental group the regenerated tissue express large amount of proteoglycans. Collage II is the most abundant collagen in hyaline cartilage and its expression characterize hyaline cartilage formation, differentiating it from bone and fibrous tissue formation. In the control group almost no collaged II expression was detected at the damaged area, suggesting differentiation to fibrotic scar tissue, whilst in the experimental group high expression of collagen II was detected. Histological and immunohistochemical analyses suggest that rHAM⁺ induced regeneration of hyaline cartilage, though it seems that the regeneration process would have further continued beyond the 12 weeks period of the experiment.

Figure 7A:
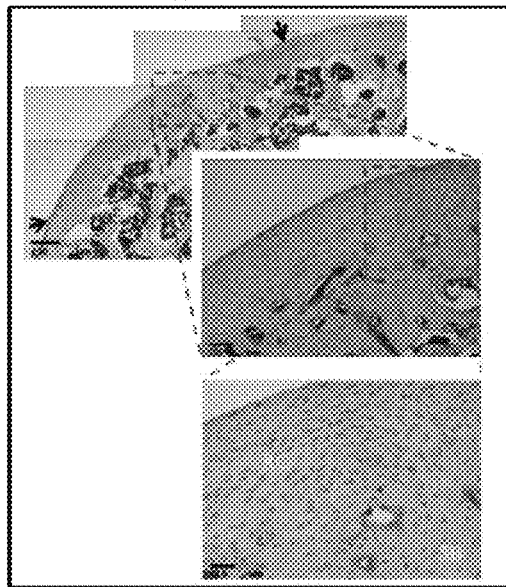
Figure 7B:
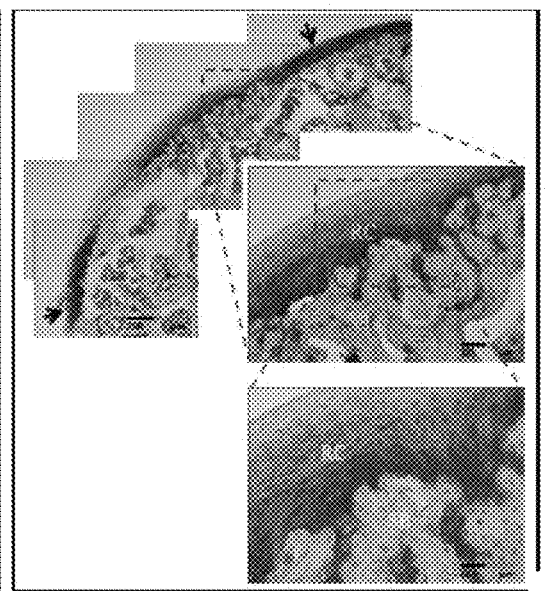
Figure 7C:
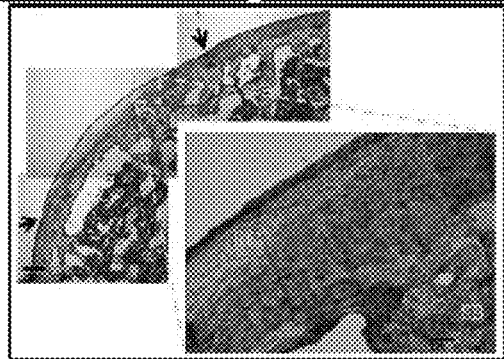

FIGS. 7A-C are enlargements of the figures presented in FIG. 6C, illustrating the regeneration of knee hyaline cartilage 12 weeks after creation of defect and application of 0.5 mg/ml rHAM⁺. (A)—Hematoxylline & Eosin staining, (B)—Toluidine Blue Staining (specific staining for glucoseaminoglycans and proteoglycans), (C)—Immunohistochemistry using Collagen II antibodies, all indicating that morphologically, the regeneration process and production of hyaline cartilage was initiated at the deeper layer and progressed towards the surface. SB—Subchondral Bone; RC—Regenerating cartilage; Arrows mark the borders of defect.

Figure 8A:
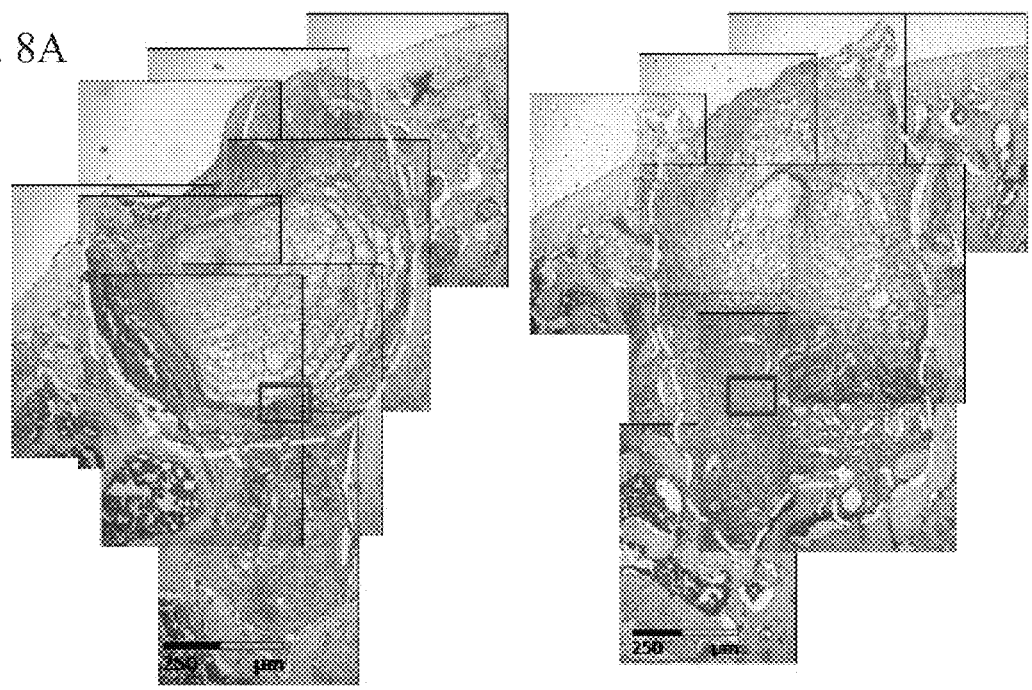
Figure 8B:
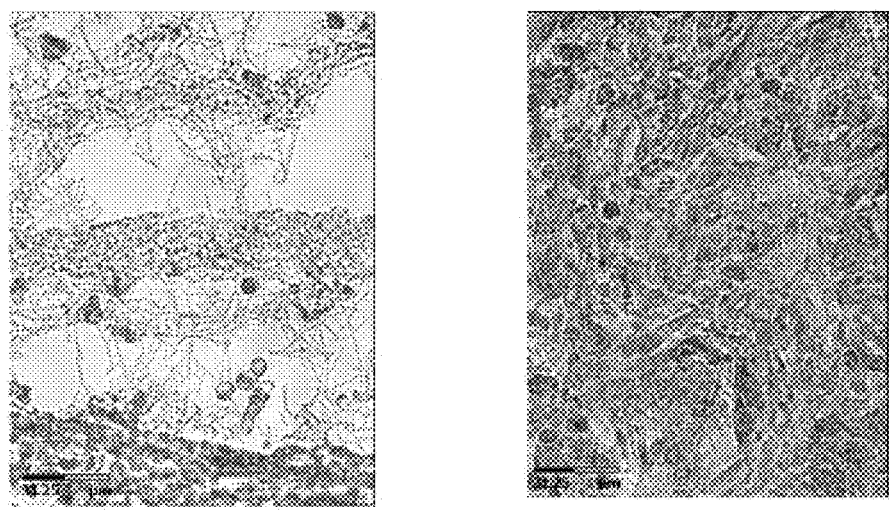

FIGS. 8A-B are photographs illustrating immunohistochemical staining of the mesenchymal stem cell marker CD 105 (brown staining) in the arranging hematoma four days after fracture creation. (A)—The dotted yellow line marks the edges of fracture, and the red square represents the area magnified in FIG. 8B. (B)—The fracture site of the experimental group, treated with 0.5 µg/µl rHAM⁺, was much more cellular, and many more CD105 positive cells were present in the arranging hematoma. In the control the fracture site was less cellular and the quantity of CD105 positive cells was much lower.

FIGS. 9A-F are photographs of histological analysis using H&E, toluidine blue and safranin-o staining, comparing the structure and polysaccharides amount (toluidine blue and safranin-o) in the knee articular cartilage of wild type (WT) mice to the amelogenin knock-out mice (KO). In the KO articular cartilage large erosions are seen involving significant parts of the weight bearing zones. It seems that there is a destruction and separation of the superficial and proliferating layers from the hypertrophic layer. While in the age-matched group of WT mice seldom small erosions were noticed (F-femur, T-tibia, M-meniscus).

Figure 10:
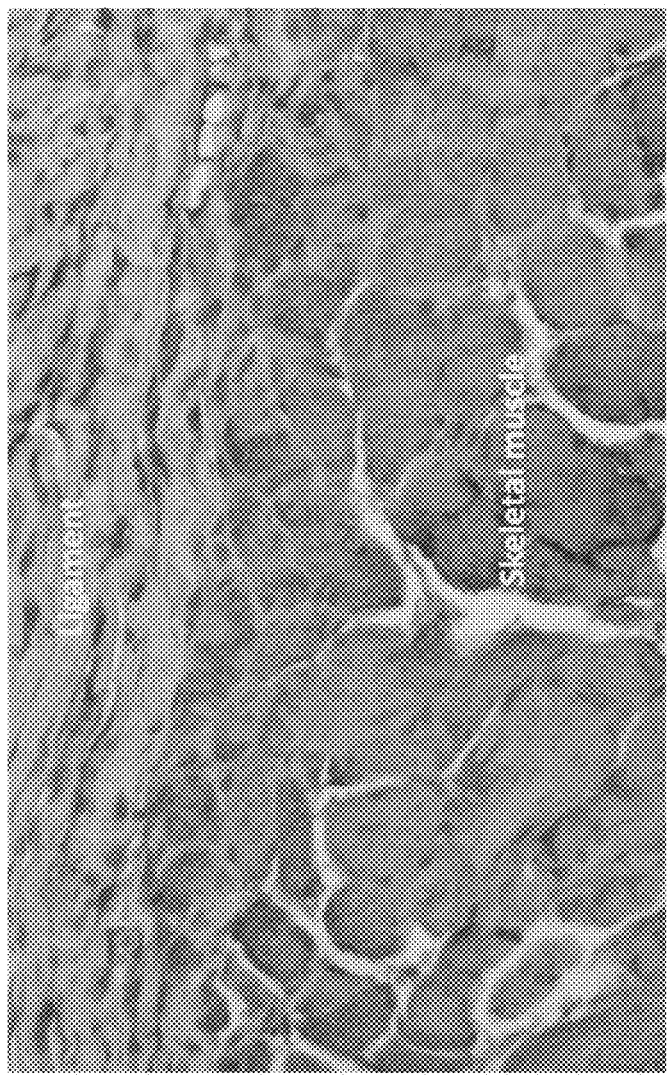

FIG. 10 is a photograph illustrating immunohistochemical analysis of rat skeletal muscle with monoclonal anti-human ameloganin antibody. The brown staining indicates amelogenin expression in the fibers of rat skeletal muscle.

Figure 11:

FIG. 11 is a photograph illustrating immunohistochemical analysis of mouse E9 (embryonic day 9) heart with anti-human amelogenin antibody. The red staining indicates amelogenin expression in the mouse E9 embryo heart. Arrow indicates the myocardium.

DESCRIPTION OF SPECIFIC EMBODIMENTS OF THE INVENTION

The present invention, in some embodiments thereof, relates to the use of amelogenin for enhancing the regeneration of hyaline cartilage, and more specifically articular cartilage.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The amelogenins are a major component of the developing extracellular enamel matrix proteins, produced by the ameloblast cells and play a major role in the biomineralization and structural organization of enamel (Robinson et al. 1998). The human amelogenin gene contains 7 exons, which undergo alternative mRNA splicing. The most abundant amelogenin lacks the internal region encoded by exon 4, is termed HX175 in human, which corresponds to isoform M180 in mice. The relatively large number of amelogenin alternatively spliced mRNA translated polypeptides and the fact that amelogenin is expressed in different tissues (calcifying and soft tissues) and of different embryonic origin, possibly reflect different functions of amelogenin.

The present inventors have now found that amelogenin may be used to enhance regeneration of articular cartilage.

Local administration of recombinant human amelogenin following injury to the osteochondral fracture site (OCF) in the articular cartilage enhanced regeneration of the tissue in a rat model (FIGS. 6A-C to 8A-B), and prevented the deterioration towards osteoarthritis, as seen in the control. This was verified by histological analysis using Hematoxylin & Eosin staining toluidine blue staining and collagen 2 staining.

Further corroboratory data for using amelogenin for the treatment of articular cartilage injuries is provided in FIGS. 9A-F which shows that amelogenin knock-out mice (KO) have lesions in the articular cartilage resembling severe osteoarthritic changes.

Thus, according to one aspect of the present invention there is provided a method of treating an injury to hyaline cartilage in a subject in need thereof, comprising administering to the subject a therapeutically effective amount of amelogenin, thereby treating the injury to the hyaline cartilage, and preventing destruction of the joint by osteoarthritic changes.

As used herein, the term "amelogenin" refers to any one of the alternatively spliced variants of the mammalian amelogenin polypeptide (e.g., human, rat, mouse amelogenin) which exhibits an amelogenin activity, e.g. enhancement of mesenchymal tissue regeneration.

The GenPept REFSEQ numbers for the 3 alternative protein isoforms of amelogenin are set forth in NP_001133.1, NP_872621.1, NP_872622.1.

The GeneBank REFSEQ transcripts for amelogenin for the 3 human alternative transcripts are set forth in NM_001142.2, NM_182680.1 and NM_182681.1. Additional cDNA sequences (also including protein sequence) include: GeneBank AF436849.1; BC069118.1; BC074951.2; M86932.1 and 567147.1.

Further details of the protein are further disclosed in Taylor et al., (2006) Protein expression and Purification 45; 43-53, the contents of which are incorporated herein by reference.

An amelogenin of the present invention also refers to homologs (e.g., polypeptides which are at least 50%, at least 55%, at least 60%, at least 65%, at least 70%, at least 75%, at least 80%, at least 85%, at least 87%, at least 89%, at least 91%, at least 93%, at least 95% or more say 100% homologous to the amelogenin sequences described above (e.g. SEQ ID NO: 1) as determined using BlastP software of the National Center of Biotechnology Information (NCBI) using default parameters). The homolog may also refer to a deletion, insertion, or substitution variant, including an amino acid substitution, thereof and biologically active polypeptide fragments thereof.

The amelogenin of this aspect of the present invention is typically generated by expressing the protein from an expression construct in an appropriate cell system.

The expression construct of the present invention preferably includes a polynucleotide sequence encoding the amelogenin under control of a transcriptional regulatory sequence (e.g. a promoter).

The phrase "an isolated polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

The expression construct can be designed as a gene knock-in construct in which case it will lead to genomic integration of construct sequences, or it can be designed as an episomal expression vector.

In any case, the expression construct can be generated using standard ligation and restriction techniques, which are well known in the art (see Maniatis et al., in: Molecular Cloning: A Laboratory Manual, Cold Spring Harbor Laboratory, New York, 1982). Isolated plasmids, DNA sequences, or synthesized oligonucleotides are cleaved, tailored, and relegated in the form desired.

Promoters suitable for use with the present invention may be constitutive, tissue specific or regulatable (e.g. comprise response elements capable for directing transcription of the polynucleotide sequence so as to confer regulatable synthesis of the amelogenin).

Constitutive promoters suitable for use with some embodiments of the invention are promoter sequences which are active under most environmental conditions and most types of cells such as the cytomegalovirus (CMV) and Rous sarcoma virus (RSV).

A suitable response element for use in regulatable promoters can be, for example, a tetracycline response element (such as described by Gossen and Bujard (Proc. Natl. Acad. Sci. USA 89:5547-551, 1992); an ectysone-inducible response element (No D et al., Proc Natl Acad Sci USA. 93:3346-3351, 1996) a metal-ion response element such as described by Mayo et al. (Cell. 29:99-108, 1982); Brinster et al. (Nature 296:39-42, 1982) and Searle et al. (Mol. Cell. Biol. 5:1480-1489, 1985); a heat shock response element such as described by Nouer et al. (in: Heat Shock Response, ed. Nouer, L., CRC, Boca Raton, Fla., pp 167-220, 1991); or a hormone response element such as described by Lee et al. (Nature 294:228-232, 1981); Hynes et al. (Proc. Natl. Acad. Sci. USA 78:2038-2042, 1981); Klock et al. (Nature 329: 734-736, 1987); and Israel and Kaufman (Nucl. Acids Res. 17:2589-2604, 1989).

The expression construct of the present invention may also include one or more enhancers. Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

Polyadenylation sequences can also be added to the expression construct in order to increase the translation efficiency of the enzyme expressed from the expression construct of the present invention. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for the present invention include those derived from SV40.

In addition to the elements already described, the expression construct of the present invention may typically contain other specialized elements intended to increase the level of expression of cloned polynucleotides or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The expression construct may or may not include a eukaryotic replicon. If a eukaryotic replicon is present, then the vector is amplifiable in eukaryotic cells using the appropriate selectable marker. If the construct does not comprise a eukaryotic replicon, no episomal amplification is possible. Instead, the recombinant DNA integrates into the genome of the engineered cell, where the promoter directs expression of the desired polynucleotide.

Examples for mammalian expression constructs include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression constructs containing regulatory elements from eukaryotic viruses such as retroviruses can also be used by the present invention. SV40 vectors include pSVT7 and pMT2. Vectors derived from bovine papilloma virus include pBV-1MTHA, and vectors derived from Epstein Bar virus include pHEBO, and p205. Other exemplary vectors include pMSG, pAV009/A$^+$, pMTO10/A$^+$, pMAMneo-5, baculovirus pDSVE, and any other vector allowing expression of proteins under the direction of the SV-40 early promoter, SV-40 later promoter, metallothionin promoter, murine mammary tumor virus promoter, Rous sarcoma virus promoter, polyhedrin promoter, or other promoters shown effective for expression in eukaryotic cells.

Viruses are specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by the present invention will depend on the cell type transformed. The ability to select suitable vectors according to the cell type transformed is well within the capabilities of the ordinary skilled artisan and as such no general description of selection consideration is provided herein. For example, bone marrow cells can be targeted using the human T cell leukemia virus type I (HTLV-I).

Recombinant viral vectors (e.g. adenoviruses or lentiviruses) are useful for in vivo expression of transgenic polynucleotides since they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

A variety of prokaryotic or eukaryotic cells can be used as host-expression systems to express the amelogenin of the present invention. These include, but are not limited to, microorganisms, such as bacteria transformed with a recombinant bacteriophage DNA, plasmid DNA or cosmid DNA expression vector containing the polypeptide coding sequence; yeast transformed with recombinant yeast expression vectors containing the polypeptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the polypeptide coding sequence.

Preferably non-bacterial expression systems are used (e.g. mammalian expression systems such as CHO cells) to express the polypeptide of the present invention since it is preferred that the polypeptides of the present invention are glycosylated.

In bacterial systems, a number of expression vectors can be advantageously selected. When large quantities of amelogenin are desired, vectors that direct the expression of high levels of the protein product, possibly as a fusion with a hydrophobic signal sequence, which directs the expressed product into the periplasm of the bacteria or the culture medium where the protein product is readily purified may be desired. Certain fusion protein engineered with a specific cleavage site to aid in recovery of the polypeptide may also be desirable. Such vectors adaptable to such manipulation include, but are not limited to, the pET series of E. coli expression vectors [Studier et al., Methods in Enzymol. 185:60-89 (1990)].

In yeast, a number of vectors containing constitutive or inducible promoters can be used, as disclosed in U.S. Pat. No. 5,932,447. Alternatively, vectors can be used which promote integration of foreign DNA sequences into the yeast chromosome.

In cases where plant expression vectors are used, the expression of the polypeptide coding sequence can be driven by a number of promoters. For example, viral promoters such as the 35S RNA and 19S RNA promoters of CaMV [Brisson et al., Nature 310:511-514 (1984)], or the coat protein promoter to TMV [Takamatsu et al., EMBO J. 6:307-311 (1987)] can be used. Alternatively, plant promoters can be used such as, for example, the small subunit of RUBISCO [Coruzzi et al., EMBO J. 3:1671-1680 (1984); and Brogli et al., Science 224:838-843 (1984)] or heat shock promoters, e.g., soybean hsp17.5-E or hsp17.3-B [Gurley et al., Mol. Cell. Biol. 6:559-565 (1986)]. These constructs can be introduced into plant cells using Ti plasmid, Ri plasmid, plant viral vectors, direct DNA transformation, microinjection, electroporation and other techniques well known to the skilled artisan. See, for example, Weissbach & Weissbach [Methods for Plant Molecular Biology, Academic Press, NY, Section VIII, pp 421-463 (1988)]. Other expression systems such as insects and mammalian host cell systems, which are well known in the art, can also be used by the present invention.

It will be appreciated that other than containing the necessary elements for the transcription and translation of the inserted coding sequence (encoding the polypeptide), the expression construct of the present invention can also include sequences engineered to optimize stability, production, purification, yield or activity of the expressed polypeptide.

Various methods can be used to introduce the expression vector of the present invention into the host cell system. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Transformed cells are cultured under effective conditions, which allow for the expression of high amounts of recombinant polypeptide. Effective culture conditions include, but are not limited to, effective media, bioreactor, temperature, pH and oxygen conditions that permit protein production. An effective medium refers to any medium in which a cell is cultured to produce the recombinant polypeptide of the present invention. Such a medium typically includes an aqueous solution having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes and petri plates. Culturing can be carried out at a temperature, pH and oxygen content appropriate for a recombinant cell. Such culturing conditions are within the expertise of one of ordinary skill in the art.

Depending on the vector and host system used for production, the ameogenin of the present invention may either remain within the recombinant cell, secreted into the fermentation medium, secreted into a space between two cellular membranes, such as the periplasmic space in *E. coli*; or retained on the outer surface of a cell or viral membrane.

Following a predetermined time in culture, recovery of the amelogenin is effected.

The phrase "recovering the amelogenin" used herein refers to collecting the whole fermentation medium containing the amelogenin and need not imply additional steps of separation or purification.

Thus, amelogenins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

To facilitate recovery, the expressed coding sequence can be engineered to encode the amelogenin fused to a cleavable moiety. Such a fusion protein can be designed so that the polypeptide can be readily isolated by affinity chromatography; e.g., by immobilization on a column specific for the cleavable moiety. Where a cleavage site is engineered between the polypeptide and the cleavable moiety, the polypeptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

The amelogenin is preferably retrieved in "substantially pure" form.

As used herein, the phrase "substantially pure" refers to a purity that allows for the effective use of the amelogenin in the applications described herein.

In addition to being synthesizable in host cells, the amelogenin can also be synthesized using in vitro expression systems. These methods are well known in the art and the components of the system are commercially available.

As well as administering a subject with amelogenin, it will be appreciated that cells (such as mesenchymal stem cells, MSCs) may be transformed so as to express amelogenin and the cells may be used to treat the injury.

The term "mesenchymal stem cell" or "MSC" is used interchangeably for adult cells which are not terminally differentiated, which can divide to yield cells that are either stem cells, or which, irreversibly differentiate to give rise to cells of a mesenchymal cell lineage e.g., adipose, osseous, cartilaginous, elastic and fibrous connective tissues, myoblasts, as well as to tissues other than those originating in the embryonic mesoderm (e.g., neural cells) depending upon various influences from bioactive factors such as cytokines.

MSC cultures utilized by some embodiments of the invention preferably include three groups of cells which are defined by their morphological features: small and agranular cells (referred to as RS-1, hereinbelow), small and granular cells (referred to as RS-2, hereinbelow) and large and moderately granular cells (referred to as mature MSCs, hereinbelow). The presence and concentration of such cells in culture can be assayed by identifying a presence or absence of various cell surface markers, by using, for example, immunofluorescence, in situ hybridization, and activity assays.

When MSCs are cultured under the culturing conditions of some embodiments of the invention they exhibit negative staining for the hematopoietic stem cell markers CD34, CD11B, CD43 and CD45. A small fraction of cells (less than 10%) are dimly positive for CD31 and/or CD38 markers.

According to a preferred embodiment of this aspect of the present invention, the mesenchymal stem cells are human.

According to another embodiment of this aspect of the present invention, the mesenchymal stem cells are isolated from newborn humans.

According to still another embodiment of this aspect of the present invention, the mesenchymal stem cells are autologous to the patient being treated.

According to still another embodiment of this aspect of the present invention, the mesenchymal stem cells are non-autologous (allergenic) to the patient being treated.

The mesenchymal stem cells may be derived from various tissues including but not limited to bone marrow, peripheral blood, placenta (e.g. fetal side of the placenta), cord blood, umbilical cord, amniotic fluid and from adipose tissue.

A method of enriching for mesenchymal stem cells from peripheral blood is described by Kassis et al [Bone Marrow Transplant. 2006 May; 37(10):967-76]. A method of isolating mesenchymal stem cells from placental tissue is described by Zhang et al [Chinese Medical Journal, 2004, 117 (6):882-887]. Methods of enriching for adipose tissue, placental and cord blood mesenchymal stem cells are described by Kern et al [Stem Cells, 2006; 24:1294-1301].

Bone marrow can be isolated from the iliac crest (or other bone) of an individual by aspiration. Low-density BM mononuclear cells (BMMNC) may be separated by a FICOL-PAQUE density gradient or by elimination of red blood cells using Hetastarch (hydroxyethyl starch). Preferably, mesenchymal stem cell cultures are generated by diluting BM aspirates (usually 20 ml) with equal volumes of Hank's balanced salt solution (HBSS; GIBCO Laboratories, Grand Island, N.Y., USA) and layering the diluted cells over about 10 ml of a Ficoll column (Ficoll-Paque; Pharmacia, Piscataway, N.J., USA). Following 30 minutes of centrifugation at 2,500×g, the mononuclear cell layer is removed from the interface and suspended in HBSS. Cells are then centrifuged at 1,500×g for 15 minutes and resuspended in a complete medium (MEM, a medium without deoxyribonucleotides or ribonucleotides; GIBCO); 20% fetal calf serum (FCS) derived from a lot selected for rapid growth of MSCs (Atlanta Biologicals, Norcross, Ga.); 100 units/ml penicillin (GIBCO), 100 µg/ml streptomycin (GIBCO); and 2 mM L-glutamine (GIBCO).

Adipose tissue-derived MSCs can be obtained by liposuction and mononuclear cells can be isolated manually by removal of the fat and fat cells, or using the Celution System (Cytori Therapeutics) following the same procedure as described above for preparation of MSCs.

Preferably the MSCs are at least 50% purified, more preferably at least 75% purified and even more preferably at least 90% purified.

Methods of purifying MSCs are known in the art and include for example culturing (in vitro or ex vivo) on polystyrene plastic surfaces (e.g. in a flask) by removing non-adherent cells (i.e. non-mesenchymal stem cells).

Other methods of selecting for MSCs are known in the art including for example positive selection against mesenchymal stem cell markers (e.g. CD105) and/or negative selection against hematopoietic stem and progenitor markers such as CD34, CD133, CD8, etc. Methods of determining protein cell-surface expression are well known in the art. Examples include immunological methods, such as, FACS analysis as well as biochemical methods (cell-surface labeling, e.g., radioactive, fluorescence, avidin-biotin).

Following isolation the cells are typically expanded by culturing in a proliferation medium capable of maintaining and/or expanding the isolated cells ex vivo. The proliferation medium may be DMEM, alpha-MEM or DMEM/F12. Preferably, the proliferation medium is DMEM. Preferably, the proliferation medium further comprises SPN, L-glutamine and a serum (such as fetal calf serum or horse serum).

Genetic modification of the mesenchymal stem cells is effected so that they express the polypeptide amelogenin. This is preferably effected by transforming such cells with an expression construct which is designed for expression of amelogenin, as further described herein above.

The genetically modified cells of this aspect of the present invention may be seeded on a scaffold prior to use. Alternatively, amelogenin (without cells) may be used to coat the scaffold or be incorporated into, or on the surface of, the scaffold.

As used herein, the term "scaffold" refers to a 3D matrix upon which cells may be cultured (i.e., survive and preferably proliferate for a predetermined time period).

Techniques for seeding cells onto or into a scaffold are well known in the art, and include, without being limited to, static seeding, filtration seeding and centrifugation seeding. Static seeding includes incubation of a cell-medium suspension in the presence of the scaffold under static conditions and results in non-uniformity cell distribution (depending on the volume of the cell suspension); filtration seeding results in a more uniform cell distribution; and centrifugation seeding is an efficient and brief seeding method (see for example EP19980203774).

The cells may be seeded directly onto the scaffold, or alternatively, the cells may be mixed with a gel which is then absorbed onto the interior and exterior surfaces of the scaffold and which may fill some of the pores of the scaffold. Capillary forces will retain the gel on the scaffold before hardening, or the gel may be allowed to harden on the scaffold to become more self-supporting. Alternatively, the cells may be combined with a cell support substrate in the form of a gel optionally including extracellular matrix components.

As mentioned, the amelogenin may be used for enhancing hyaline cartilage repair or regeneration.

The term "enhancing repair and or regeneration" refers one or more of the following: increase in the rate of production of new tissue, improvement in the functionality, amount or quality of the new tissue produced as compared to untreated control.

In connection with cartilage, after an injury the body usually produces a scar tissue with some characteristics of cartilage (fibrocartilage), which in some cases may enable functional joint movement (may be painful), but eventually the joint will degenerate and osteoarthritis will develop. Few types of cartilage are known. The articular hyaline cartilage, the menisceal tissue, the labrum tissue (acetabular labrum and glenoid labrum) and the intervertebral disc generally do not naturally regenerate. Regeneration of hyaline cartilage means preferential formation of functional cartilage (articular cartilage in joints) sufficient enough to enable joint function and/or to prevent further pain and destruction e.g. osteoarthritis.

Regarding menisci, most of the menisceal tears are at the white-white zone, which is an area without blood supply. Tears in this area and most of the tears in the red-white zone will not heal and partial menisectomy should be performed. Regeneration of menisci refers to formation of new menisceal cartilaginous tissue connection between the sides of a tear. It can also refer to renewal of degenerative menisceal tissue. The acetabular and glenoid labrums are fibrocartilagenous structures, which serve as static stabilizers of the hip and shoulder joints. Tears or detachment of the labrum from the bone, causes pain, disability and joint instability (mainly in the shoulder).

Regeneration of the labrum means repair of the tear or renewal of the connection to the bone. The intervertebral discs are fibrocartilagenous, with surrounding annulus fibrosus composed mainly of collagen type 1 and a softer central nucleus pulposus made mainly of type 2 collagen. The nucleus pulposus has a high content of polysaccharide and is approximately 88% water. Aging results in loss of water and conversion to fibrocartilage. Regeneration of intervertebral disc refers to closure or decrease in the size of the annulus fibrosus tear, and/or to renewal of the nucleus pulposus composition. As regards to ligament and tendon, these tissues also generally do not normally regenerate. In part, scar tissue forms, which has significantly inferior mechanical properties. Regeneration of ligament and tendon means formation of new connection between the edges of the stumps, with similar mechanical properties to the tissue prior to the injury. Muscle regeneration refers to formation of new functional connection between the edges of a torn muscle, or to renewal of functional muscular units after an insult e.g. ischemic heart attack.

The method of the invention is intended to treat conditions where ligament, tendon, cartilage, intervertebral disc, menisci, bone, cardiac muscle and skeletal muscle are damaged due to trauma or pathological conditions, including degeneration due to normal age and exercise.

For cartilage:
Various degrees of chondreal lesions.
Osteo-chondral lesions.
Chondromalacia.
Osteo-chondritis dissecans.
Osteoarthritis.
Herniated and degenerative intervertebral disc.
Degenerative intervertebral disc.
Menisceal tear.
Menisceal degeneration.
Labral tears.

Labral detachment from the bone (e.g. Bankart lesion—in the shoulder).

In any of the methods described herein, the amelogenin can be administered either per se or, (with or without cells) preferably as a part of a pharmaceutical composition that further comprises a pharmaceutically acceptable carrier.

As used herein a "pharmaceutical composition" refers to a preparation of amelogenin or cells genetically engineered to express amelogenin, with other chemical components such as pharmaceutically suitable carriers and excipients. The purpose of a pharmaceutical composition is to facilitate administration of a compound to a subject.

Hereinafter, the term "pharmaceutically acceptable carrier" refers to a carrier or a diluent that does not cause significant irritation to a subject and does not abrogate the biological activity and properties of the administered compound. Examples, without limitations, of carriers are propylene glycol alginate, saline, emulsions and mixtures of organic solvents with water.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

According to a preferred embodiment of the present invention, the pharmaceutical carrier is an aqueous solution of saline.

Techniques for formulation and administration of drugs may be found in "Remington's Pharmaceutical Sciences," Mack Publishing Co., Easton, Pa., latest edition, which is incorporated herein by reference.

Suitable routes of administration include direct administration into the tissue or organ of interest (local administration).

For example, the present invention contemplates administering the amelogenin during an arthroscopic procedure (e.g. to the knee).

For any preparation used in the methods of the invention, the therapeutically effective amount or dose can be estimated initially from in vitro and cell culture assays. Preferably, a dose is formulated in an animal model to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals.

The data obtained from these in vitro and cell culture assays and animal studies can be used in formulating a range of dosage for use in human. For example an effective concentration of amelogenin was shown to be about 0.05-5 μg in rats.

The dosage may vary depending upon the dosage form employed and the route of administration utilized. The exact formulation, route of administration and dosage can be chosen by the individual physician in view of the patient's condition, (see e.g., Fingl, et al., 1975, in "The Pharmacological Basis of Therapeutics", Ch. 1 p. 1).

For injection, the active ingredients of the pharmaceutical composition may be formulated in aqueous solutions, preferably in physiologically compatible buffers such as Hank's solution, Ringer's solution, or physiological salt buffer.

Dosage amount and interval may be adjusted individually so that sufficient amount of amelogenin reach the appropriate cells. Dosages necessary to achieve the desired effect will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or diminution of the disease state is achieved.

The amount of a composition to be administered will, of course, be dependent on the individual being treated, the severity of the affliction, the manner of administration, the judgment of the prescribing physician, etc. The dosage and timing of administration will be responsive to a careful and continuous monitoring of the individual changing condition.

The protein and/or the engineered cells may be administered to the desired site by direct application either by an injection, by arthroscopic device or during open surgery. The cells may be placed in an isolated form, or placed in a suitable medium, or in a suitable matrix including scaffold matrixes that may incorporate the cells. The cells may be administered alone or together with other compounds intended to promote activity or proliferation of MSC, or with other compounds known to enhance regeneration and/or repair of these tissues.

Since non-autologous cells are likely to induce an immune reaction when administered to the body several approaches have been developed to reduce the likelihood of rejection of non-autologous cells. These include either suppressing the recipient's immune system, providing anti-inflammatory treatment and/or encapsulating the non-autologous cells in immunoisolating, semipermeable membranes before transplantation.

Encapsulation techniques are generally classified as microencapsulation, involving small spherical vehicles and macroencapsulation, involving larger flat-sheet and hollow-fiber membranes (Uludag, H. et al. Technology of mammalian cell encapsulation. Adv Drug Deliv Rev. 2000; 42: 29-64).

Methods of preparing microcapsules are known in the arts and include for example those disclosed by Lu M Z, et al., Cell encapsulation with alginate and alpha-phenoxycinnamylidene-acetylated poly(allylamine). Biotechnol Bioeng. 2000, 70: 479-83, Chang T M and Prakash S. Procedures for microencapsulation of enzymes, cells and genetically engineered microorganisms. Mol Biotechnol. 2001, 17: 249-60, and Lu M Z, et al., A novel cell encapsulation method using photosensitive poly(allylamine alpha-cyanocinnamylidene acetate). J Microencapsul. 2000, 17: 245-51.

For example, microcapsules are prepared by complexing modified collagen with a ter-polymer shell of 2-hydroxyethyl methylacrylate (HEMA), methacrylic acid (MAA) and methyl methacrylate (MMA), resulting in a capsule thickness of 2-5 μm. Such microcapsules can be further encapsulated with additional 2-5 μm ter-polymer shells in order to impart a negatively charged smooth surface and to minimize plasma protein absorption (Chia, S. M. et al. Multi-layered microcapsules for cell encapsulation Biomaterials. 2002 23: 849-56).

Other microcapsules are based on alginate, a marine polysaccharide (Sambanis, A. Encapsulated islets in diabetes treatment. Diabetes Technol. Ther. 2003, 5: 665-8) or its derivatives. For example, microcapsules can be prepared by the polyelectrolyte complexation between the polyanions sodium alginate and sodium cellulose sulphate with the polycation poly(methylene-co-guanidine) hydrochloride in the presence of calcium chloride.

It will be appreciated that cell encapsulation is improved when smaller capsules are used. Thus, the quality control, mechanical stability, diffusion properties, and in vitro activities of encapsulated cells improved when the capsule size was reduced from 1 mm to 400 μm (Canaple L. et al., Improving cell encapsulation through size control. J Biomater Sci Polym Ed. 2002; 13:783-96). Moreover, nanoporous biocapsules with well-controlled pore size as small as 7 nm, tailored surface chemistries and precise microarchitectures were found to successfully immuno isolate microenvironments for cells (Williams D. Small is beautiful: microparticle and nanoparticle technology in medical devices. Med Device Technol. 1999, 10: 6-9; Desai, T. A. Microfabrication technology for pancreatic cell encapsulation. Expert Opin Biol Ther. 2002, 2: 633-46).

Examples of immunosuppressive agents include, but are not limited to, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE™), etanercept, TNF alpha blockers, a biological agent that targets an inflammatory cytokine, and Non-Steroidal Anti-Inflammatory Drug (NSAIDs). Examples of NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors and tramadol.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Material and Methods

Production of the Recombinant Human Amelogenin Protein rHAM$^+$:

Human amelogenin cDNA was amplified by PCR from a recombinant plasmid containing human amelogenin X cDNA (GeneBank accession no. M86932), representing the most abundant amelogenin mRNA transcript, which lacks exon 4 and codes for a 175 amino acid protein. The human cDNA was subcloned into the pFastBac™HTb vector (Invitrogen). This system adds a hexa-histidine tag to the amino terminus of the expressed protein, enabling effective one-step purification by $Ni^{2+}$-NTA affinity chromatography. The recombinant protein was expressed in *Spodoptera frugiperda* (Sf9) eukaryotic insect cells and the yield of purified human amelogenin (rHAM+) was up to 10 mg/L culture. rHAM+ was characterized by SDS-PAGE, Western blot, ESI-TOF spectrometry, peptide mapping and MS/MS sequencing (Taylor et al. 2006).

Isolation of CD105-Positive Human Mesenchymal Stem Cells (MSCs) (CD105+-hMSCs):

CD105+hBMSC from human femoral bone marrow were isolated using ficoll gradient, immunomagnetic methodology (MACS) and culturing. Analysis of mononuclear cells and fresh CD105+ cells, obtained from the same source was performed by flow cytometry (FACS) and in vitro differentiation assays (chondrogenic, osteogenic, and adipogenic differentiation).

Production of Recombinant Adenovirus-5 Constructs.

Luciferase, Beta-galactosidase, FLAG, and GFP amelogenin adenovirus were produced using the Gateway cloning system (Invitrogen), under the CMV promoter.

Engineering of the CD105+ hMSCs Using the Recombinant Adenovirus-5 Constructs.

HEK-293 cells were infected with each of the different recombinant adenoviruses (for propagation), followed by transduction into the CD105+-hMSCs. The engineered hMSCs were serially diluted to achieve 50% effective titer, for determination of viral titer (using FACS to determine the ratio of GFP-positive/negative cells, blue count for beta-gal positive/negative cells, β-gal with a nuclear localization signal, anti-adenovirus antibodies, or by plaque forming unit.

Animal Model for Torn Ligament and Tendon Repair:

Adult female Sabra rats weighing about 300 g were used in this study. Before the operation rHAM+ was dissolved in sterile aqueous solution of propylene glycol alginate carrier (PGA) at concentrations ranging from 0.05 μg/μl up to 5 μg/μl. All surgical procedures were performed under anesthesia, keeping sterile conditions. Rats were anesthetized with intraperitoneal ketamine hydrochloride (60 mg/kg) and xylazine hydrochloride (10 mg/kg). The right knee joint was approached through a medial skin incision, and the medial collateral ligament (MCL) of the rat was cut transversely, together with the fascia covering the MCL, using a microsurgical technique. After transection, in the experimental group 7 μl of rHAM+ dissolved in PGA carrier were applied to the gap between the MCL stumps. In the control group the same procedure was performed but the gap was filled with 7 μl of PGA carrier alone. The skin was stitched. Before and after the operation all animals received pain relief medication (Tramadol). All animals were monitored for signs of pain and infection. No cast or dressing was applied and the animals were allowed unrestricted cage movement. To follow the course of regeneration rats were euthanized with an overdose of ketamine and xylazine, at several intervals after the operation. The two knees (treated & untreated) from experimental rats and control rats were dissected out and prepared for mechanical testing, histological, cross polarization microscopy, immunohistochemical, confocal microscopy, in-situ hybridization and electron microscopy studies.

Animal Model for Articular Cartilage Repair:

In-order to create an accurate and reproducible model, the present inventors produced an instrument that holds the knee and produces a defect at a constant depth and size in the femoral trochlea, using a high speed bearing.

Sabra female rats, mean weight of 0.3 kg were anaesthetized with an intraperitoneal injection of ketamin and xylasin. Analgesic with Tramadol (SC) was injected before the operation. Through a medial parapatellar approach, the patella was everted to expose the articular surfaces. A full thickness osteochondral defect, sized 1.5 mm×1.5 mm and 1.8 mm deep, was created using the machine described above, on the articular cartilage of the patellar groove (trochlea) of the distal femur. Thorough irrigation of the knee with normal saline was performed. Various concentrations of rHAM+ dissolved in 2.25% PGA was applied to the defect site of the experimental knee. PGA carrier alone was applied to the knee defect of the control group. The arthrotomy was sutured with interrupted 5-0 vicryl sutures and the skin was closed with interrupted 5-0 nylon sutures. The rat received pain relief medication (SC tramadol injections) twice a day for 3 days after the operation. Clinical signs of wound infection or systemic infection were followed. The rats were weighted twice a week, to exclude a rat that develops signs of infection or decrease in weight by 10% between weighing or more than 20% from its initial weight. The rats were sacrificed by overdose injection of penthal and the chest was opened.

Evaluation of the healing of the OCD site was carried out by morphometric analysis of the defect size, and by histological analysis using hematoxylin and eosin staining (H&E), followed by computerized morphometry, immunology and other molecular and biochemical contemporary methodologies.

Hyaline Cartilage from Knee Joint of Amelogenin Wild Type and Knockout Colonies:

Amelogenin knockout mice were obtained (NIH-MMRRC: 4 carrier females and 4 normal males; amelogenin is expressed only on the X chromosome in mice). Through planned mating, a large colony of over 300 amelogenin null mice and their corresponding wild type mice was established. These two colonies were used to compare the structure and composition of the hyaline cartilage between knee joints of amelogenin knockout (KO) and wild type (WT) mice. The knee joints were harvested from 6-24 months old mice. The joint bony structure was first studied using micro-CT scans. The structure and the proteoglycans composition of the cartilage were studied by H&E, toluidine blue and safranin o-fast green staining.

Creation of Experimental Periodontitis:

8-10 week old immuno-compromised rats (150-180 gram) Nude-Hsd:RH-rnu/rnu rats were used. The operation procedure for creation of experimental periodontitis includes: Critical size periodontal defect was created in the mesial aspect of both first maxillary molars of immuno-compromised rats (Nude-Hsd:RH-rnu/rnu rats). Nylon thread ligature was placed surgically around the cervix of the treated molars. The ligature was knotted on the periodontal defect side so that it remains sub-gingivally, and supra-gingivally at the other side. One week later, the ligature was removed, granulation tissue was also removed and the exposed roots were scaled, planned and washed. The engineered cells mixed with fibrin gel, or rHAM+ dissolved in PGA, were injected into the defect.

Creation of Critical Size Defect in the Calvariae (Parietal Bone):

8-10 weeks old immuno-compromised mice Hsd:Athymic Nude-Foxn1$^{nu}$ were used. Mice are anesthetized with intraperitoneal ketamine hydrochloride (60 mg/kg) and xylazine hydrochloride (10 mg/kg). A bone critical size (diameter 5 mm) defect was created using a microsurgical technique. Engineered human bmMSCs over expressing amelogenin, in fibrin hydrogel scaffold, were applied to the site of the defect in the experimental group of mice, following which the skin was stitched.

Creation of Non-Union Segmental Fracture in the Radial Bone (Long Bone):

8-10 weeks old immuno-compromised mice Hsd:Athymic Nude-Foxn1$^{nu}$ were used. Mice were anesthetized with intraperitoneal ketamine hydrochloride (60 mg/kg) and xylazine hydrochloride (10 mg/kg). The mid-shaft of the right radius was isolated, using a microsurgical technique. Critical size (2.5 mm long) osteotomy was created at a constant area in the mid-shaft radius. Engineered human bmMSCs over expressing amelogenin, in fibrin hydrogel scaffold were applied at the site of the defect in the experimental group of mice, following which the skin was stitched.

Mechanical Testing of Normal, Torn and Regenerated Ligaments:

The bone-ligament-bone unit was gently isolated under dissecting-microscope to assure that the MCL is the only connection between the femur and tibia. The specimen was wrapped in cotton gauze soaked in normal saline solution and stored at −20° C. before testing, or was tested immediately. The bone-ligament-bone unit was fastened in a clamping device which was attached to an electrohydraulic-materials testing machine at room temperature in normal saline solution. Force-displacement curves were recorded and analyzed. Load to failure (N) (peak of the curve) was measured and was compared to the normal non-transected ligament of the same animal. The slope of the force-displacement curve is a measure of the ligament stiffness; a higher slope represents stiffer ligament and a lower slope represents a more lax ligament.

Tissue Preparation for Histology, Cross Polarization Microscopy, Immunohistochemical Analysis and Confocal Microscopy:

For histology and immunohistochemistry the entire ligament tissue was cut from the bone and fixed in 4% Para-Formaldehyde (PFA) for 24 hours at 4° C. The region of the regenerating tissues was studied. More details are described in Haze et al. 2007; Haze et al. 2009.

Determination of the Degree of Regeneration and the Characterization of the Regenerated Tissues and Ectopically Formed Tissues with Time:

This was carried out using micro-CT, histology, immunohistochemistry, in-situ hybridization, quantitative-PCR, confocal microscopy, Western blot, and various biochemical assays (e.g. alkaline phosphatase etc.), and molecular biology techniques aimed at identification of phenotypes of the regenerated tissues. The spatio-temporal distribution of the engineered CD105$^+$-hMSCs in the regenerating tissues and neighboring tissues was monitored by the detection of the various fused amelogenin proteins. Markers for the specific cells such as bone, PDL, cementum, fat, muscle were tested. The emerging results reveal: 1. The general pattern and extent of regeneration of the different tissues. 2. Comparison between the different inducing platforms—amelogenin engineered cell based regeneration versus amelogenin protein induction. 3. Possible functions of amelogenin and basic mechanisms, e.g. autocrine and paracrine influence of amelogenin, cell signaling activity, etc.

Indirect Immunohistochemistry:

Performed using the Zymed laboratories inc. kit protocol. Controls comprise of pre-immune sera or PBS. Various amelogenin antibodies (monoclonal and polyclonal) and antibodies against other proteins (e.g. specific mesenchymal cell markers (such as CD105, CD73, CD90, STRO-1, osteocalcin, BMP2, BSP, etc.) were used.

Colocalization of Amelogenin with Cell-Specific Markers Using Confocal Microscopy:

Double immunofluorescence staining reactions using mouse amelogenin monoclonal antibody and polyclonal antibody against known cell-specific markers was performed. The second fluorescent antibodies used were Alexa Fluor 488 (green) goat anti-mouse IgG (for amelogenin) and Alexa Fluor 647 (red) goat anti-rabbit IgG (for the cell markers). In addition to the spatial-temporal expression of different types of recruited, proliferating and differentiating cells, this method also allows colocalization of amelogenin expression and the expression of these cell markers.

In-Situ Hybridization (ISH):

RNA-probes (antisense and sense) were purchased or produced from rat cDNA. ISH was performed using DIG RNA labeling kit and InnoGenex universal ISH protocol.

Isolation and Sequencing of Amelogenin mRNA from the Regenerating Tissues, and Ectopic Tissues:

Regenerating tissues were dissected, RNA samples isolated, and RT is performed using Cells-to-cDNA Kit. PCR reactions were performed using specific amelogenin primers and primers for various cell markers.

Quantitative PCR: To compare specific patterns of gene expression at different stages of regeneration/ectopic tissue formation, quantitative PCR was employed, using Taqman probes and 7300 Real time PCR system (Applied Biosystems).

In-Vivo DiI and DiO Labeling of Cells Surrounding the Defect:

Labeling with DiI and DiO (two different fluorescent colors) was performed during the operation prior to application of rHAM$^+$ or MSCs engineered to overexpress amelogenin. The purpose of adding DiI/DiO was to mark the exact location of the defect. The other fluorescent label was used to mark migration of MSCs from distant locations or to colocalize amelogenin or other osteogenic/chondrogenic etc. markers. Colocalization was performed using confocal microscopy.

Tracking MSC Recruitment:

The IVIS kinetic (Caliper) was used for in-vivo tracking of cell recruitment to the defect site, induced by recombinant human amelogenin (rHAM$^+$).

Example 1

Repair/Regeneration of Torn Ligament and Tendon

Two weeks following the transection of the medial collateral ligament (MCL), the gap between the MCL stumps could clearly be seen in the control group (PGA carrier alone). In the experimental group, the gap was closed and the MCL stumps could not be detected (FIGS. 1A-D).

The biomechanical properties of the torn MCL 12 weeks after transection were tested, using increasing concentrations of recombinant human amelogenin (0.1 µg/µl, 0.5 µg/µl, 1 µg/µl, 2.5 µg/µl, 5 µg/µl) and in cohorts of about 15 rats in each group. As illustrated in FIGS. 2A-B for rHAM$^+$ concentration of 0.5 µg/µl, mechanical restoration of the transected MCL was observed after a single application of the recombinant human amelogenin. FIGS. 3A-C illustrate that the histology of the transected MCL of the experimental group (i.e. 12 weeks after application of amelogenin) is more similar to control non-transected ligaments, whereas the histology of the transected MCL in the absence of amelogenin is more similar to scar tissue.

Immunohistochemical studies show that there is more collagen 1 expression in the experimental ligament as compared to the control PGA treated ligament after 12 weeks. Collagen 1 is the major protein in ligament which provides the mechanical properties and strength of normal ligament (FIGS. 4A-C). Further, immunohistochemical studies show that four days after transaction more cells which express CD105 are detected in the filled gap of the experimental ligament as compared to the number of cells which express CD105 in the filled gap of the control ligament (FIGS. 5A-C), indicating that in the experimental ligament there is increased recruitment of mesenchymal stem cells (MSCs).

Example 2

Amelogenin for Aiding Regeneration of Articular Cartilage Repair/Regeneration of Osteochondreal Defect Model 12 weeks after creation of osteochondreal fracture (OCF) at the trochlea of the rat, morphometric analysis demonstrated that the size of the fracture was reduced significantly in the groups treated with various concentrations of recombinant human amelogenin (rHAM$^+$) dissolved in PGA carrier (experimental), as compared to the size of the defect in the group treated with PGA carrier only (control; FIGS. 6A-C, 7A-C). Furthermore, the size of the osteochondreal damage in the femoral trochlea of the control group (treated with PGA carrier only) was increased and degenerative changes were seen in large areas of the articular surface, resembling osteoarthritic changes. In the experimental knee the changes were much more limited and the OCF was filled with tissue that was similar in its structural and its biochemical composition to hyaline cartilage.

Indirect immunohistochemistry illustrates that after 4 days there are significantly more cells expressing CD105 in the experimental tissues as compared to the control tissues (FIGS. 8A-B).

Complete Lack of Amelogenin Cause Progressive Destruction of Articular Cartilage:

In order to evaluate amelogenin function in articular cartilage biology, the present inventors compared the structure and composition of the articular cartilage in normal wild type mice to amelogenin knock-out mice. Preliminary results show that in aging amelogenin knock-out (KO) mice (1.5-2 years old) there is an increase in cartilage destruction, typical to osteoarthritis, as compared to wild type (WT) mice. Large erosions are seen in the articular cartilage involving significant parts of the weight bearing zones. It seems that in KO mice there is a destruction and separation of the superficial and proliferating layers from the hypertrophic layer, while in the age-matched group of WT mice seldom small erosions are noticed (FIGS. 9A-F).

Example 3

Amelogenin Expression in Muscle

As illustrated in FIGS. 10 and 11, amelogenin is expressed in both skeletal (FIG. 10) and cardiac (FIG. 11) muscle.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

1. Aslan H, Zilberman Y, Kandel L, Liebergall M, Oskouian R. J, Gazit D, Gazit Z, 2006. Osteogenic Differentiation of Noncultured Immunoisolated Bone Marrow-Derived CD105$^+$ Cells. STEM CELLS 24, 7: 1728-1737.
2. Bhosale A M and Richardson J B, 2008. *Articular cartilage: structure, injuries and review of management*. British Medical Bulletin; 87: 77-95.
3. Bi Y, Ehirchiou D, Kilts T M, Inkson C A, Embree M C, Sonoyama W, Li L, Leet A I, Seo B M, Zhang L, Shi S, Young M F (2007) Identification of tendon stem/progenitor cells and the role of the extracellular matrix in their niche. Nat Med 13:1219-1227.
4. Deutsch D, Haze-Filderman A, Blumenfeld A, Dafni L, Leiser Y, Shay B, Gruenbaum-Cohen Y, Rosenfeld E, Fermon E, Zimmermann B, Haegewald S, Bernimoulin J P, Taylor A L. *Amelogenin, a major structural protein in mineralizing enamel, is also expressed in soft tissues: brain and cells of the hematopoietic system*. Eur J Oral Sci. 2006; 114: 183-9.
5. Gruenbaum-Cohen Y, Tucker A S, Haze A, Shilo D, Taylor A L, Shay B, Sharpe P T, Mitsiadis T A, Ornoy A, Blumenfeld A, Deutsch D, 2008. *Amelogenin in craniofacial development: the tooth as a model to study the role of amelogenin during embryogenesis*. J Exp Zoolog B Mol Dev Evol. 15:445-57.
6. Haze A, Taylor A L, Haegewald S, Leiser Y, Shay B, Rosenfeld E, Gruenbaum-Cohen Y, Dafni L, Zimmerman B, Heikinheimo K, Gibson C W, Fisher L W, Young M A, Blumenfeld A, Bernimoulin J P, Deutsch D, 2009. *Regeneration of bone and periodontal ligament induced by Recombinant amelogenin after periodontitis*. J Cell Mol Med. 13:1110-24.
7. Haze A, Taylor A L, Blumenfeld A, Rosenfeld E, Leiser Y, Dafni L, Shay B, Gruenbaum-Cohen Y, Fermon E, Haegewald S, Bernimoulin J P, Deutsch D, 2007. *Amelogenin expression in long bone and cartilage cells and in bone marrow progenitor cells*. Anat Rec (Hoboken). 290:455-60.
8. Hoffmann A, Gross G, 2007. Tendon and ligament engineering in the adult organism: mesenchymal stem cells and gene-therapeutic approaches. Int Orthop 31:791-797.
9. Kawasaky K, Sugihara S, Nishida K, Ozaki T, Yoshida A, Ohtsuka A and Inoue A, 2004. Hoechst 33342 is a useful cell tracer for long-term investigation of articular cartilage repair. Arch Histol Cytol 67: 13-19.
10. Kawaguchi H, Hirachi A, Hasegawa N, Iwata T, Hamaguchi H, Shiba H, Takata T, Kato Y, Kurihara H, 2004. Enhancement of periodontal tissue regeneration by transplantation of bone marrow mesenchymal stem cells. *J Periodontol.* 75; 1281-1287.

11. Moutsatsos I K, Turgeman G, Zhou S, Kurkalli B G, Pelled G, Tzur L, Kelley P, Stumm N, Mi S, Miller R, Zilberman Y, Gazit D, 2001. Exogenously regulated stem cell-mediated gene therapy for bone regeneration. *Mol Ther.* 3; 449-461.
12. Robinson C, Brookes S J, Shore R C, Kirkham J, 1998. *The developing enamel matrix: nature and function*. Eur J Oral Sci 106; 1:282-291.
13. Shapiro J L, Wen X, Okamoto C T, Wang H J, Lyngstadaas S P, Goldberg M, Snead M L, Paine M L, 2007. *Cellular uptake of amelogenin, and its localization to CD63, and Lamp1-positive vesicles*. Cell Mol Life Sci. 64: 244-56.
14. Taylor A L, Haze-Filderman A, Blumenfeld A, Shay B, Dafni L, Rosenfeld E, Leiser Y, Fermon E, Gruenbaum-Cohen Y, Deutsch D, 2006. *High yield of biologically active recombinant human amelogenin using the baculovirus expression system*. Protein Expr Purif.; 45: 43-53.
15. Tei K, Matsumoto T, Mifune Y, Ishida K, Sasaki K, Shoji T, Kubo S, Kawamoto A, Asahara T, Kurosaka M, Kuroda R (2008) Administrations of peripheral blood CD34-positive cells contribute to medial collateral ligament healing via vasculogenesis. Stem Cells 26:819-830.
16. Zou Y, Wang H, Shapiro J L, Okamoto C T, Brookes S J, Lyngstadaas S P, Snead M L, Paine M L, 2007. *Determination of protein regions responsible for interactions of amelogenin with CD63 and LAMP1*. Biochem J.; 408: 347-54.

What is claimed is:

1. A method of regenerating functional hyaline cartilage in a subject suffering from damage to hyaline cartilage, comprising administering to the site of damage a therapeutically effective amount of an amelogenin polypeptide having the amino acid sequence as set forth in SEQ ID NO:1, thereby regenerating functional hyaline cartilage.

2. The method of claim 1, wherein said mammalian amelogenin polypeptide is the human amelogenin polypeptide.

3. The method of claim 2, wherein said amelogenin polypeptide consists of an amino acid sequence as set forth in SEQ ID NO: 1.

4. The method of claim 1, wherein the damage is due to a tear.

5. The method of claim 1, wherein said amelogenin polypeptide is a recombinant amelogenin.

6. The method of claim 1, wherein said amelogenin polypeptide is administered endoscopically.

7. The method of claim 1, wherein the subject is one suffering from damage to hyaline cartilage in which said damage is caused by trauma.

8. The method of claim 1, wherein the subject is one suffering from damage to hyaline cartilage in which said damage is caused by a pathological condition.

9. The method of claim 1, wherein the subject is one suffering from damage to hyaline cartilage, which damage is manifested by osteoarthritis.

SEQUENCE LISTING

```
<160> NUMBER OF SEQ ID NOS: 1

<210> SEQ ID NO 1
<211> LENGTH: 175
<212> TYPE: PRT
<213> ORGANISM: Homo sapiens

<400> SEQUENCE: 1

Met Pro Leu Pro Pro His Pro Gly His Pro Gly Tyr Ile Asn Phe Ser
1               5                   10                  15

Tyr Glu Val Leu Thr Pro Leu Lys Trp Tyr Gln Ser Ile Arg Pro Pro
                20                  25                  30

Tyr Pro Ser Tyr Gly Tyr Glu Pro Met Gly Gly Trp Leu His His Gln
            35                  40                  45

Ile Ile Pro Val Leu Ser Gln Gln His Pro Pro Thr His Thr Leu Gln
        50                  55                  60

Pro His His His Ile Pro Val Val Pro Ala Gln Gln Pro Val Ile Pro
65                  70                  75                  80

Gln Gln Pro Met Met Pro Val Pro Gly Gln His Ser Met Thr Pro Ile
                85                  90                  95

Gln His His Gln Pro Asn Leu Pro Pro Pro Ala Gln Gln Pro Tyr Gln
            100                 105                 110

Pro Gln Pro Val Gln Pro Gln Pro His Gln Pro Met Gln Pro Gln Pro
        115                 120                 125

Pro Val His Pro Met Gln Pro Leu Pro Pro Gln Pro Pro Leu Pro Pro
    130                 135                 140

Met Phe Pro Met Gln Pro Leu Pro Pro Met Leu Pro Asp Leu Thr Leu
145                 150                 155                 160

Glu Ala Trp Pro Ser Thr Asp Lys Thr Lys Arg Glu Glu Val Asp
                165                 170                 175
```

10. The method of claim 1, wherein the subject is one suffering from damage to hyaline cartilage, which damage is degeneration of hyaline cartilage due to normal age and exercise.

11. The method of claim 1, wherein said hyaline cartilage comprises articular cartilage.

* * * * *